(12) United States Patent
Ruchti et al.

(10) Patent No.: US 7,039,446 B2
(45) Date of Patent: *May 2, 2006

(54) INDIRECT MEASUREMENT OF TISSUE ANALYTES THROUGH TISSUE PROPERTIES

(75) Inventors: Timothy L. Ruchti, Gilbert, AZ (US); Thomas B. Blank, Chandler, AZ (US); Alexander D. Lorenz, Chandler, AZ (US); Stephen L. Monfre, Gilbert, AZ (US); Kevin H. Hazen, Gilbert, AZ (US); Suresh N. Thennadil, New Castle upon Tyne (GB)

(73) Assignee: Sensys Medical, Inc., Chandler, AZ (US)

( * ) Notice: Subject to any disclaimer, the term of this patent is extended or adjusted under 35 U.S.C. 154(b) by 262 days.

This patent is subject to a terminal disclaimer.

(21) Appl. No.: 10/349,573

(22) Filed: Jan. 22, 2003

(65) Prior Publication Data
US 2004/0127777 A1    Jul. 1, 2004

Related U.S. Application Data

(63) Continuation-in-part of application No. 10/297,736, filed as application No. PCT/US02/02288 on Jan. 25, 2002.

(60) Provisional application No. 60/382,433, filed on May 20, 2002, provisional application No. 60/363,345, filed on Mar. 8, 2002, provisional application No. 60/264,431, filed on Jan. 26, 2001.

(51) Int. Cl.
*A61B 5/00* (2006.01)

(52) U.S. Cl. ...................... 600/310; 600/316

(58) Field of Classification Search ............ 600/310, 600/316, 317, 322, 323, 407, 437, 438, 473, 600/476
See application file for complete search history.

(56) References Cited

U.S. PATENT DOCUMENTS 5,487,384 A * 1/1996 Lee .......................... 600/316

(Continued)

OTHER PUBLICATIONS

Helwig, AM; Arnold, MA; Small, GW; Evaluation of Kromoscopy: Resolution of glucose and urea, Applied Optics 2000 39, 4715-4720.

(Continued)

*Primary Examiner*—Eric F. Winakur
(74) *Attorney, Agent, or Firm*—Michael A. Glenn; Glenn Patent Group

(57) ABSTRACT

Methods and system for noninvasive determination of tissue analytes utilize tissue properties as reflected in key features of an analytical signal to improve measurement accuracy and precision. Physiological conditions such as changes in water distribution among tissue compartments lead to complex alterations in the measured analytical signal of skin, leading to a biased noninvasive analyte measurement. Changes in the tissue properties are detected by identifying key features in the analytical signal responsive to physiological variations. Conditions not conducive to the noninvasive measurement are detected. Noninvasive measurements that are biased by physiological changes in tissue are compensated. In an alternate embodiment, the analyte is measured indirectly based on natural physiological response of tissue to changes in analyte concentration. A system capable of such measurements is provided.

92 Claims, 4 Drawing Sheets

U.S. PATENT DOCUMENTS

| | | | |
|---|---|---|---|
| 5,551,422 A * | 9/1996 | Simonsen et al. | 600/322 |
| 6,002,953 A | 12/1999 | Bock | |
| 6,044,285 A | 3/2000 | Chaiken et al. | 600/316 |
| 6,049,727 A | 4/2000 | Crothall | 600/310 |
| 6,049,728 A | 4/2000 | Chou | |
| 6,119,026 A | 9/2000 | McNulty et al. | 600/310 |
| 6,125,297 A | 9/2000 | Siconolfi | |
| 6,216,022 B1 | 4/2001 | Tyrrell et al. | 600/310 |
| 6,280,381 B1 | 8/2001 | Malin et al. | |
| 6,377,828 B1 | 4/2002 | Chaiken et al. | |

OTHER PUBLICATIONS

Heise HM, Marbach R, Koschinsky TH, Gries FA. "Non-invasive blood glucose sensors based on near-infrared spectroscopy," Artif Org 1994;18:439-47.

T.B. Blank, T.L. Ruchti, S.F. Malin and S.L. Monfre, "The use of near-infrared diffuse reflectance for the non-invasive prediction of blood glucose," IEEE Lasers and electro-optics society newsletter, vol. 13, Num. 5, Oct. 1999.

Jagemann KU, Fischbacker C, Danzer K, Muller UA, Mertes B. "Application of near-infrared spectroscopy for non-invasive determination of blood/tissue glucose using neural network," Z Phys Chem 1995;191S:179-190.

Robinson MR, Eaton RP, Haaland DM, Keep GW, Thomas EV, Stalled BR, Robinson PL. "Non-invasive glucose monitoring in diabetic patients: A preliminary evaluation," Clin Chem 1992;38:1618-22.

Klonoff, D.C., "Mid-Infrared Spectroscopy for Noninvasive Blood Glucose Monitoring," IEEE Lasers and electro-optics society newsletter, vol. 12, No. 2, Apr. 1998.

P. Zheng, P., C.E. Kramer, C.W. Barnes, J.r. Braig, B.B. Sterling, "Noninvasive Glucose Determination by Oscillating Thermal Gradient Spectrometry," Diabetes Technology & Therapeutics, vol. 2, No. 1, pp. 17-25, 2000.

Shichiri, M., T. Uemura, K. Nishida, "Non-invasive Fourier Transformed Infrared Spectroscopy for the Measurement of Submucosal Tissue Glucose Concentration," IEEE Lasers and electro-optics society newsletter, vol. 12, No. 2, Apr. 1998.

Bittner, A., H.M. Heise, Th. Koschinsky, F.A. Gries, "Evaluation of Microdialysis and FT-IR ATR-spectroscopy for in-vivo Blood Glucose Monitoring," Mikrochim. Acta [suppl.] 14. 827-828 (1997).

Khalil OS. "Spectroscopic and clinical aspects of non-invasive glucose measurements," Clin Chem 1999;45:165-77.

S.Y. Wang, C.E. Hasty, P.A. Watson, J.P. Wickstead, R.D. Stith and W.F. March, "Analysis of Metabolites in Aqueous Solutions Using Laser Raman Spectroscopy," Applied Optics, vol. 32, No. 6, pp. 925-929.

Cote, G.L., "Noninvasive Optical Glucose Sensing—An Overview," J. Clin. Eng., pp. 253-259, Jul./Aug. 1997.

Waynant, R.W. and V.M. Chenault, "Overview of Non-Invasive Fluid Glucose Measurement Using Optical Techniques to Maintain Glucose Control in Diabetes Mellitus," IEEE Lasers and electro-optics society newsletter, vol. 12, No. 2, Apr. 1998.

Heise, H.M., "Near-Infrared Spectrometry for in vivo Glucose Sensing," in Biosensors in the Body: Continuous in vivo Monitoring, Ed. D.M. Fraser: John Wiley & Sons, 1997.

Bruulsema, J.T., J.E. Hayward, T.J. Farrell, M.S. Patterson, L. Heinemann, M. Berger, M. Koschinsky, J. Sandani-Christiansen, H. Orskov, M. Essenprels, G. Schmeizelsen-Redeker and D. Böcker, "Correlation between blood glucose concentration in diabetics and noninvasively measured tissue optical scattering coefficient," Optics Letters, vol. 22, No. 3, Feb. 1, 1997, pp. 190-182.

* cited by examiner

INDIRECT MEASUREMENT OF TISSUE ANALYTES THROUGH TISSUE PROPERTIES

CROSS REFERENCE TO RELATED APPLICATIONS

This application claims benefit of U.S. Provisional Patent Application Ser. Nos. 60/382,433, filed May 20, 2002 and 60/363,345, filed Mar. 8, 2002; and is a Continuation-in-part of U.S. patent application Ser. No. 10/297,736, filed on Oct. 27, 2003, claiming priority from PCT Application No. PCT/US02/02288, filed Jan. 25, 2002, which claims benefit of U.S. Provisional Patent Application Ser. No. 60/264,431, filed on Jan. 26, 2001.

BACKGROUND OF THE INVENTION

1. Field of the Invention

The invention generally relates to the field of biomedical testing. More particularly, the present invention relates to methods and apparatus for noninvasive tissue analyte determination.

2. Description of Related Art

Noninvasive Measurement of Glucose

Diabetes is a leading cause of death and disability worldwide and afflicts an estimated sixteen million Americans. Complications of diabetes include heart and kidney disease, blindness, nerve damage, and high blood pressure with the estimated total cost to United States economy alone exceeding $90 billion per year [Diabetes Statistics, Publication No. 98-3926, National Institutes of Health, Bethesda Md. (November 1997)]. Long-term clinical studies show that the onset of complications can be significantly reduced through proper control of blood glucose concentrations [The Diabetes Control and Complications Trial Research Group, *The effect of intensive treatment of diabetes on the development and progression of long-term complications in insulin-dependent diabetes mellitus*, N Eng J of Med, 329:977–86 (1993)]. A vital element of diabetes management is the self-monitoring of blood glucose levels by diabetics in the home environment. A significant disadvantage of current monitoring techniques is that of poor compliance due to the inconvenient and painful nature of drawing blood through the skin prior to analysis. Additionally, current glucose monitoring techniques involve the added cost of a disposable, one-use-only, test strip that is an additional and significant impediment to regular monitoring.

For the above reasons, new methods for self-monitoring of blood glucose levels are required to improve the prospects for more rigorous control of blood glucose in diabetic patients. A noninvasive glucose monitor addresses this problem and represents a significant and widely recognized advancement over the current state-of-the-art by eliminating the puncture wound used for drawing blood, the biohazard related to the invasive blood draw and the use of test strips.

Numerous approaches have been proposed for measuring blood glucose levels non-invasively, including:

Kromoscopy [see A. Helwig, M. Arnold, G. Small; *Evaluation of Kromoscopy: Resolution of glucose and urea*, Applied Optics, 39:4715–4720 (2000)];

Near-infrared Spectroscopy [see T. Blank, T. Ruchti, S. Malin and S. Monfre, *The use of near-infrared diffuse reflectance for the non-invasive prediction of blood glucose*, IEEE Lasers and electro-optics society newsletter, v.13:5 (October 1999); and R. Robinson, R. Eaton, D. Haaland, G. Keep, E. Thomas, B. Stalled, P. Robinson, *Non-invasive glucose monitoring in diabetic patients: A preliminary evaluation*, Clin Chem, 38:1618–22 (1992)];

Mid-Infrared Spectroscopy [see D. Klonoff, *Mid-infrared Spectroscopy for Noninvasive Blood Glucose Monitoring*, IEEE Lasers and electro-optics society newsletter, v.12:2 (April 1998)];

ATR (attenuated total reflectance);

Oscillating Thermal Gradient Spectrometry; [P. Zheng, C. Kramer, C. Barnes, J. Braig, B. Sterling, *Noninvasive glucose determination by oscillating thermal gradient spectrometry*, Diabetes Technology & Therapeutics, v.2:1, pp. 17–25 (2000)];

Far infra-red radiation spectroscopy;

Radio wave impedance;

Polarimetry;

Infrared and FT-IR Spectroscopy [see M. Shichiri, T. Uemura, K. Nishida, *Non-invasive Fourier transformed infrared spectroscopy for the measurement of submucosal tissue glucose concentration*, IEEE Lasers and Electro-optics Society Newsletter, v.12:2 (April 1998); and A. Bittner, H. Heise, T. Koschinsky, F. Gries, *Evaluation of microdialysis and FT-IR ATR-spectroscopy for in-vivo blood glucose monitoring*, Mikrochim. Acta [suppl.] 14:827–828 (1997)];

IR transmission [see M. Block, *Noninvasive IR transmission measurement of analyte in the tympanic membrane*, U.S. Pat. No. 6,002,953 (Dec. 14, 1999)];

Fluorescence (illuminescense) spectrometry;

Raman spectroscopy [see J. Chaiken, C. Peterson, *Method for non-invasive measurement of an analyte*, U.S. Pat. No. 6,377,828 (Apr. 23, 2002)];

Photoacoustic and pulse laser photoacoustic spectroscopy [see M. Chou, *Method and apparatus for noninvasive measurement of blood glucose by photoacoustics*, U.S. Pat. No. 6,049,728 (Apr. 11, 2000)];

Near-Infrared Scattering;

Emission spectroscopy;

Passive IR spectroscopy;

Bioelectric impedance or potentiometry, bioelectrical response spectroscopy; [see S. Siconolfi, *Body Fluids Monitor*, U.S. Pat. No. 6,125,297 (Sep. 26, 2000)]

Ultrasound;

Visible spectroscopy; and

Far infrared spectroscopy.

Each method has associated advantages and disadvantages, but to date, no noninvasive technique for the self-monitoring of blood glucose has been certified by the United States Food and Drug Administration (USFDA). Consequently, an FDA approved product for consumer use based on any one of these technologies for the purpose of diabetes management through non-invasive glucose monitoring is not available. While the reasons impeding the progress of the various non-invasive technologies are diverse, a common and fundamental problem to these methods is the dynamic and diverse nature of the targeted tissue used to extract the information necessary to measure glucose [see O. Khalil, *Spectroscopic and clinical aspects of non-invasive glucose measurements*, Clin Chem, 45:165–77(1999); and S. Malin, T. Ruchti, *An intelligent system for noninvasive blood analyte prediction*, U.S. Pat. No. 6,280,381 (Aug. 28, 2001); and T. Blank, T. Ruchti, S. Malin and S. Monfre, *The use of near-infrared diffuse reflectance for the non-invasive prediction of blood glucose*, IEEE Lasers and Electro-Optics Society Newsletter, v.13:5, (October 1999); and G. Cote, *Noninvasive optical glucose sensing—an overview*, J. Clin.

Eng., pp. 253–259 (July/August 1997); and R. Waynant, V. Chenault, *Overview of non-invasive fluid glucose measurement using optical techniques to maintain glucose control in diabetes mellitus*, IEEE Lasers and electro-optics society newsletter, v.12:2 (April 1998); and H. Heise, *Near-infrared Spectrometry for in vivo glucose sensing, in Biosensors in the Body: Continuous In Vivo Monitoring*, D. Fraser, ed., John Wiley & Sons (1997)]. While each targets a modification to a particular excitation or probing signal by the concentration or presence of glucose, the interfering substances, constituents, and dynamic properties of tissue together with the trace level of glucose have rendered the goal of creating a reliable device elusive. Thus, it would be a significant technical advance to provide a method foe measuring glucose non-invasively that overcomes these pervasive problems.

EXAMPLE

Non-invasive glucose measurement using a near-infrared analyzer generally involves the illumination of a small region on the body with near-infrared electromagnetic radiation (light in the wavelength range 700–2500 nm). The light is partially absorbed and partially scattered according to its interaction with the constituents of the tissue prior to being reflected back to a detector. The detected light contains quantitative information that corresponds to the known interaction of the incident light with components of the body tissue including water, fat, protein, and glucose.

Previously reported methods for the noninvasive measurement of glucose through near-infrared spectroscopy rely on the detection of the magnitude of light attenuation caused by the absorption signature of glucose as represented in the targeted tissue volume. For example, in G. Petrovsky, M. Slavin, L. Slavina, N. Izvarina, M. Pankevich, *Apparatus and method for noninvasive glucose measurement*, U.S. Pat. No. 6,097,975 (Aug. 1, 2000), a narrow bandwidth of light is selected for noninvasive glucose measurement based upon where glucose is known to absorb. The tissue volume constitutes the portion of irradiated tissue from which light is diffusely reflected or transmitted to the spectrometer detection system. The signal due to the absorption of glucose is extracted from the spectral measurement through various methods of signal processing and one or more mathematical models. The models are developed through the process of calibration based on an exemplary set of spectral measurements and associated reference blood glucose values (the calibration set) obtained from an analysis of capillary (fingertip) or venous blood.

Near-infrared spectroscopy has been applied in specific studies for the noninvasive measurement of blood glucose levels. M. Robinson, R. Eaton, D. Haaland, G. Keep, E. Thomas, B. Stalled, P. Robinson, *Noninvasive glucose monitoring in diabetic patients: A preliminary evaluation*, Clin Chem., 38:1618–22 (1992) reports three different instrument configurations for measuring diffuse transmittance through the finger in the 600–1300 nm range. Meal tolerance tests were used to perturb the glucose levels of three subjects and calibration models were constructed specific to each subject on single days and tested through cross-validation. Absolute average prediction errors ranged from 19.8 to 37.8 mg/dL. [see H. Heise, R. Marbach, T. Koschinsky, F. Gries, *Noninvasive blood glucose sensors based on near-infrared spectroscopy*, Artif Org, 18:439–47 (1994); and H. Heise, R. Marbach, *Effect of data pretreatment on the noninvasive blood glucose measurement by diffuse reflectance near-IR spectroscopy*, SPIE Proc, 2089:114–5 (1994); R. Marbach, T. Koschinsky, F. Gries, H. Heise, *Noninvasive glucose assay by near-infrared diffuse reflectance spectroscopy of the human inner lip*, Appl Spectrosc, 47:875–81 (1993) and R. Marbach, H. Heise, *Optical diffuse reflectance accessory for measurements of skin tissue by near-infrared spectroscopy*, Applied Optics 34(4):610–21 (1995) present results through a diffuse reflectance measurement of the oral mucosa in the 1111–1835 nm range with an optimized diffuse reflectance accessory. In-vivo experiments were conducted on single diabetics using glucose tolerance tests and on a population of 133 different subjects. The best standard error of prediction reported was 43 mg/dL and was obtained from a two-day single person oral glucose tolerance test that was evaluated through cross-validation.

K. Jagemann, C. Fischbacker, K. Danzer, U. Muller, B. Mertes, *Application of near-infrared spectroscopy for noninvasive determination of blood/tissue glucose using neural network*, Z Phys Chem, 191S:179–190 (1995); C. Fischbacker, K. Jagemann, K. Danzer, U. Muller, L. Papenkrodt, J. Schuler, *Enhancing calibration models for noninvasive near-infrared spectroscopic blood glucose determinations*, Fresenius J Anal Chem 359:78–82 (1997); K. Danzer, C. Fischbacker, K. Jagemann, K. Reichelt, *Near-infrared diffuse reflection spectroscopy for noninvasive blood-glucose monitoring*, LEOS Newsletter 12(2):9–11 (1998); and U. Muller, B. Mertes, C. Fischbacker, K. Jagemann, K. Danzer, *Noninvasive blood glucose monitoring by means of new infrared spectroscopic methods for improving the reliability of the calibration models*, Int J Artif Organs, 20:285–290 (1997) recorded spectra in diffuse reflectance over the 800–1350 nm range on the middle finger of the right hand with a fiber-optic probe. Each experiment involved a diabetic subject and was conducted over a single day with perturbation of blood glucose levels through carbohydrate loading. Results, using both partial least squares regression and radial basis function neural networks were evaluated on single subjects over single days through cross-validation. Danzer, et al., supra, report an average root mean square prediction error of 36 mg/dL through cross-validation over 31 glucose profiles.

J. Burmeister, M. Arnold, G. Small, *Human noninvasive measurement of glucose using near infrared spectroscopy* [abstract], Pittcon, New Orleans La. (1998) collected absorbance spectra through a transmission measurement of the tongue in the 1429–2000 nm range. A study of five diabetic subjects was conducted over a 39-day period with five samples taken per day. Every fifth sample was used for an independent test set and the standard error of prediction for all subjects was greater than 54 mg/dL.

In T. Blank et al., supra, the reported studies demonstrate noninvasive measurement of blood glucose during modified oral glucose tolerance tests over a short time period. The calibration was customized for the individual and tested over a relatively short time period.

In all of these studies, limitations were identified that would affect the acceptance of such a method as a commercial product. These limitations included sensitivity, sampling problems, time lag, calibration bias, long-term reproducibility, and instrument noise. Fundamentally, however, accurate noninvasive estimation of blood glucose is presently limited by the available near-infrared technology, the trace concentration of glucose relative to other constituents, the small analytical signal related to glucose, and the dynamic nature of the skin and living tissue of the patient [see Khalil, supra]. As reported by Malin, et al., supra the entirety of which is hereby incorporated by reference, chemical, structural, and physiological variations occur that produce dramatic and nonlinear changes in the optical properties of the tissue sample [see R. Anderson, J. Parrish, *The optics of human skin*, Journal of Investigative Dermatology, 7:1, pp. 13–19 (1981), W. Cheong, S. Prahl, A. Welch, *A review of the optical properties of biological tissues*, IEEE Journal of Quantum Electronics, 26:12, pp. 2166–2185, (December 1990); D. Benaron, D. Ho, *Imaging (NIRI) and quantitation (NIRS) in tissue using time-resolved spectrophotometry: the impact of statically and dynamically variable optical path lengths*, SPIE, 1888, pp. 10–21 (1993), J. Conway, K. Norris, C. Bodwell, *A new approach for the estimation of body composition: infrared interactance*, The American Journal of Clinical Nutrition, 40, pp. 1123–1140 (December 1984), S. Homma, T. Fukunaga, A. Kagaya, *Influence of adipose tissue thickness in near infrared spectroscopic signals in the measurement of human muscle*, Journal of Biomedical Optics, 1:4, pp. 418–424 (October 1996), A. Profio, *Light transport in tissue*, Applied Optics, 28:12), pp. 2216–2222, (June 1989), M. Van Gemert, S. Jacques, H. Sterenborg, W. Star, *Skin optics*, IEEE Transactions on Biomedical Engineering, 36:12, pp. 1146–1154 (December 1989), and B. Wilson, S. Jacques, *Optical reflectance and transmittance of tissues: principles and applications*, IEEE Journal of Quantum Electronics, 26:12, pp. 2186–2199].

Glucose measurement is further complicated by the heterogeneity of the sample, the multi-layered structure of the skin, the rapid variation related to hydration levels, changes in the volume fraction of blood in the tissue, hormonal stimulation, temperature fluctuations, and blood analyte levels. This can be further considered through a discussion of the scattering properties of skin.

Tissue Scattering Properties

Skin Structure

The structure and composition of skin varies widely among individuals, between different sites within an individual, and over time on the same individual. Skin includes a superficial layer known as the stratum corneum, a stratified cellular epidermis; and an underlying dermis of connective tissue. Below the dermis is the subcutaneous fatty layer or adipose tissue. The epidermis, with a thickness of 10–150 µm, together with the stratum corneum provides a barrier to infection and loss of moisture and other body constituents, while the dermis is the thick inner layer that provides mechanical strength and elasticity [F. Ebling, The Normal Skin, *Textbook of Dermatology*, $2^{nd}$ ed.; A. Rook; D. Wilkinson, F. Ebling, Eds.; Blackwell Scientific, Oxford, pp 4–24 (1972)]. In humans, the thickness of the dermis ranges from 0.5 mm over the eyelid to 4 mm on the back and averages approximately 1.2 mm over most of the body [S. Wilson, V. Spence, Phys. Med. Biol., 33:894–897 (1988)].

In the dermis, water accounts for approximately 70% of the volume. The next most abundant constituent is collagen, a fibrous protein comprising 70–75% of the dry weight of the dermis. Elastin fibers, also a protein, are plentiful though they constitute only a small proportion of the bulk. In addition, the dermis contains a wide variety of structures (e.g., sweat glands, hair follicles, and blood vessels) and other cellular constituents [see F. Ebling, supra]. Conversely, the subcutaneous layer (adipose tissue) is by volume approximately 10% water and consists primarily of cells rich in triglycerides or fat. The concentration of glucose varies in each layer according to a variety of factors which include the water content, the relative sizes of the fluid compartments, the distribution of capillaries, the perfusion of blood, the glucose uptake of cells, the concentration of glucose in blood, and the driving forces (e.g. osmotic pressure) behind diffusion. Due to the high concentration of fat, the average concentration of water soluble glucose in subcutaneous tissue is significantly lower than that of the dermis.

Properties of Skin

Non-invasive technologies, such as those listed previously, measure the alteration of a probing or excitation signal (e.g., near-infrared radiation, emitted radiation from the body, radio wave, etc.) by specific properties of tissue (e.g., absorption, scattering, impedance, optical rotation, fluorescence, etc.). However, other sample constituents of tissue often interfere and the specific response (the alternation of the probing or excitation signal) due to glucose is greatly attenuated or completely obscured.

For example, one may consider the measurement of glucose through near-infrared spectroscopy on the basis of the absorption of glucose. In a near-infrared absorption spectrum, a change in the concentration of glucose is reflected by a change in the absorption of light according to the absorption and scattering properties of glucose. However, in addition to the effect of glucose on the near-infrared light (the probing signal) that is delivered to the skin, the probing signal is also reflected, diffusely reflected, transmitted, scattered, and absorbed in a complex manner related to the structure and composition of the tissue. When near-infrared light is delivered to the skin, a percentage of it is reflected, while the remainder penetrates into the skin. The proportion of reflected light, or specular reflectance is typically between 4–7% of the delivered light over the entire spectrum from 250–3000 nm (for a perpendicular angle of incidence) [J. Parrish, R. Anderson, F. Urbach, D. Pitts, *UV-A: Biologic Effects of Ultraviolet Radiation with Emphasis on Human Responses to Longwave Ultraviolet*, New York, Plenum Press (1978)]. The 93–96% of the incident light that enters the skin is attenuated due to absorption and scattering within the many layers of the skin. These two processes, combined with orientation of the sensors of the spectrometer instrument, determine the tissue volume irradiated by the source and "sampled" through the collection of diffusely reflected light.

Diffuse reflectance or remittance is defined as that fraction of incident optical radiation that is returned from a turbid sample. Alternately, diffuse transmittance is the fraction of incident optical radiation that is transmitted through a turbid sample. Absorption by the various skin constituents mentioned above accounts for the spectral extinction of the light within each layer. Scattering is the only process by which the beam may be returned to contribute to the diffuse reflectance of the skin. Scattering also has a strong influence on the light that is diffusely transmitted through a portion of the skin.

The scattering of light in tissues is in part due to discontinuities in the refractive index on the microscopic level, such as the aqueous-lipid membrane interfaces between each tissue compartment or the collagen fibrils within the extracellular matrix [B. Wilson, S. Jacques, *Optical reflectance and transmittance of tissues: principles and applications*, IEEE Journal of Quantum Electronics, 26:12 (December 1990)]. The spatial distribution and intensity of scattered light depends upon the size and shape of the particles relative to the wavelength, and upon the difference in refractive index between the medium and the constituent particles. The scattering of the dermis is dominated by the scattering from collagen fiber bundles in the 2.8 µm diameter range occupying twenty-one percent of the dermal volume, and the refractive index mismatch is 1.38/1.35 [S. Jacques, *Origins of tissue optical properties in the UVA, Visible and NIR Regions*, Optical Society of America, Topical Meeting, Orlando Fla. (Mar. 18–22, 1996)]. The spectral characteristics of diffuse remittance from tissue result from a complex interplay of the intrinsic absorption and scattering properties of the tissue, the distribution of the heterogeneous scattering components and the geometry of the point(s) of irradiation relative to the point(s) of light detection.

The near-infrared absorption of light in tissue is primarily due to three fundamental constituents: water, protein, and fat. As the main constituent, water dominates the near-infrared absorbance above 1100 nm and is observed through pronounced absorbance bands at 1450, 1900, and 2600 nm (see, for example, FIG. 1). Protein in its various forms, in particular, collagen is a strong absorber of light that irradiates the dermis. Near-infrared light that penetrates to subcutaneous tissue is absorbed primarily by fat. In the absence of scattering, the absorbance of near-infrared light due to a particular analyte, A, can be approximated by Beer's Law at each wavelength by:

$$A = \epsilon c l \quad (1)$$

where a the analyte specific absorption coefficient, c is the concentration and l is the pathlength. The overall absorbance at a particular wavelength is the sum of the individual absorbances of each particular analyte given by Beer's Law. The concentration of a particular analyte, such as glucose, can be determined through a multivariate analysis of the absorbance over a multiplicity of wavelengths because a is unique for each analyte. However, in tissue compartments expected to contain glucose, the concentration of glucose is at least three orders of magnitude less than that of water. Given the known extinction coefficients of water and glucose, the signal targeted for detection by reported approaches to near-infrared measurement of glucose (the absorbance due to glucose in the tissue) is expected to be, at most, three orders of magnitude less than other interfering tissue constituents. Therefore, the near-infrared measurement of glucose requires a high level of sensitivity over a broad wavelength range. Multivariate analysis is often utilized to enhance sensitivity.

In addition, the diverse scattering characteristics of the skin (e.g., multiple layers and heterogeneity) cause the light returning from an irradiated sample to vary in a highly nonlinear manner with respect to tissue analytes, in particular, glucose. Simple linear models, such as Beer's Law have been reported to be invalid for the dermis [R. Anderson, J. Parrish, *The optics of human skin*, Journal of Investigative Dermatology, 77:1, pp. 13–19 (1981).]. Such nonlinear variation is a recognized problem and several reports have disclosed unique methods for compensating for the nonlinearity of the measurement while providing the necessary sensitivity [see S. Malin, et al., supra; E. Thomas, R. Rowe, *Methods and apparatus for tailoring spectroscopic calibration Models*, U.S. Pat. No. 6,157,041 (Dec. 5, 2000).].

Dynamic Properties of the Skin

While knowledge of and utilization of the properties of the skin, high instrument sensitivity, and compensation for inherent nonlinearities are all vital to the application of non-invasive technologies in blood analyte measurement, an understanding of the biological and chemical mechanisms that lead to time dependent changes in the properties of skin tissue is equally important and, yet, largely ignored. At a given measurement site, skin tissue is often assumed to remain static, except for changes in the target analyte and other interfering species. However, variations in the physiological state and fluid distribution of tissue profoundly affect the optical properties of tissue layers and compartments over a relatively short period of time. Such variations are often dominated by fluid compartment equalization through water shifts and are related to hydration levels and changes in blood analyte levels.

Total body water accounts for over 60% of the weight of the average person and is distributed between two major compartments: the intracellular fluid (two-thirds of total body water) and the extracellular fluid (one-third of total body water) [see A. Guyton, J. Hall, *Textbook of Medical of Physiology*, $9^{th}$ ed., Philadelphia, W. B. Saunders Company (1996)]. The extracellular fluid in turn is divided into the interstitial fluid (extravascular) and the blood plasma (intravascular). Water-permeable lipid membranes separate the compartments and water is transferred rapidly between them through the process of diffusion in order to equalize the concentrations of water and other analytes across the membrane. The net water flux from one compartment to another constitutes the process of osmosis and the amount of pressure required to prevent osmosis is termed the osmotic pressure. Under static physiological conditions the fluid compartments are at equilibrium. However, during a net fluid gain or loss as a result of water intake or loss, all compartments gain or lose water proportionally and tend towards a constant relative volume.

An important mechanism for distributing substances contained in blood serum that are needed by the tissues, such as water and glucose, is through the process of diffusion. The invention recognizes that Fick's law of diffusion drives the short-term intra-/extra vascular fluid compartment balance. The movement of water and other analytes from intravascular to extravascular compartments occurs rapidly as tremendous numbers of molecules of water and other constituents, in constant thermal motion, diffuse back and forth through the capillary wall. It has been reported that the rate at which water molecules diffuse through the capillary membrane is about eighty times greater than the rate at which the plasma itself flows linearly along the capillary [see Guyton, et al., supra, p. 164]. That is, the water of the plasma is exchanged with the water of the interstitial fluid 80 times before the plasma can transverse the entire distance of the capillary. In the Fick's Law expression, the actual diffusion flux $I_{OA}$ is proportional to the concentration gradient, $dC/dx$ between the two compartments and the diffusivity of the molecule, $D_A$ according to the equation:

$$I_{OA} = -D_A \left( \frac{dC}{dx} \right) \quad (2)$$

Short term increases (or decreases) in blood glucose concentrations lead to an increase (or decrease) in blood osmolality (number of molecules per unit mass of water). Fluid is rapidly redistributed accordingly and results in a change in the water concentration of each body compartment. For example, the osmotic effect of hyperglycemia is a movement of intravascular water to the extravascular space. Conversely, a decrease in blood glucose concentration leads to a movement of water to intravascular space from the extravascular compartment.

Because the cell membrane is relatively impermeable to most solutes but highly permeable to water, whenever there is a higher concentration of a solute on one side of the cell membrane, water diffuses across the membrane toward the region of higher solute concentration. Large osmotic pressures can develop across the cell membrane with relatively small changes in the concentration of solutes in the extracellular fluid. As a result, relatively small changes in concentration of impermeable solutes in the extracellular fluid, such as glucose, can cause tremendous changes in cell volume.

The Problem

Redistribution of water between various tissue compartments alters the properties of the tissue through a diversity of changes including, but not limited to, changes in:

the water concentration;
the concentration of other analytes;
the scattering of skin;
the absorbance of skin;
the electrical resistance;
the refractive indices of various layers;
the thickness of tissue layers, the impedance of tissue;
the emitted radiation from the body, the mechanical properties of tissue; and
the size and distribution of scattering centers.

Therefore, the properties of the tissue sample are modified in a highly nonlinear and profound manner. In addition, the effective tissue volume and its composition, sampled by each technology, are varied. Consequently, the property measurement varies in a complex manner that is incompatible with current modes of glucose detection. As an example, one might consider the case of near-infrared spectroscopy applied to non-invasive measurement of glucose. When glucose varies, the absorption and scattering properties of tissue vary in a manner reflecting the resulting redistribution of water among the various tissue compartments. Therefore, a near-infrared measurement of glucose based upon the absorption due to the glucose molecules present in the sampled tissue volume is significantly biased by changes in the effective pathlength, the tissue volume, and the relative concentration of interfering analytes (i.e., water).

A few methods are reported to compensate in some part for the dynamic variation of the tissue although none address the problem cited above. For example, several reported methods of noninvasive glucose measurement develop calibration models that are specific to an individual over a short period of time [see Robinson, et al., supra; Burmeister et al., supra; Blank et al., supra; K. Hazen, *Glucose determination in biological matrices using near-infrared spectroscopy*, Doctoral Dissertation, University of Iowa (August, 1995); and J. Burmeister, *In vitro model for human noninvasive blood glucose measurements*, Doctoral Dissertation, University of Iowa (December 1997)]. This approach avoids modeling the differences between patients and therefore cannot be generalized to more individuals. This approach also fails to address the prevalent short-term problem related to physiologically induced variation and no means of compensating for variation related to the dynamic water shifts of fluid compartments is reported.

S. Malin et al., supra, report a method for compensating for variation related to the structure and state of the tissue through an intelligent pattern recognition system capable of determining calibration models that are most appropriate for the patient at the time of measurement. The calibration models are developed from the spectral absorbance of a representative population of patients that have been segregated into groups. The groups or classes are defined on the basis of structural and state similarity such that the variation within a class is small compared to the variation between classes. Classification occurs through extracted features of the tissue absorbance spectrum related to the current patient state and structure.

Thomas, et al., supra, identifies a method for reducing intra-subject variation through the process of mean-centering both the instrument response and target analyte. However, this method does not address the key problem of short term physiological and chemical changes related to the dynamic nature of the tissue nor the intra-patient variation related to the heterogeneity of the tissue sample.

What has not previously been contemplated is a means of compensating for the changes in tissue properties resulting from the dynamic chemical, physical, and physiological response of the body and its tissues to changes in analyte concentration, and/or using such changes in tissue properties as the basis of noninvasive analyte measurement.

Specifically, the alteration of water distribution among the various tissue and body compartments as a result of changes in glucose concentration has not been identified, measured, and used for either compensation of or the basis for analyte measurement. As a result, noninvasive measurement of glucose is limited by the dynamic nature of tissue related to the tissue's physiological response to various conditions and the redistribution of water among tissue fluid compartments.

In view of the problems left unsolved by the prior art, there exists a need for a method and apparatus to:

first, detect changes in the chemical and physical properties of the tissue due to the changing physiology of the subject, specifically changes related to water shifts between tissue compartments;

second, use these features to determine conditions unsuitable for glucose measurement through non-invasive technologies; and finally, either use the features to compensate for the changing properties of the tissue or alternately, utilize the properties and features to measure glucose.

SUMMARY OF THE INVENTION

The invention provides methods and a system for noninvasively measuring key constituents and properties of tissue and the extraction from an analytical signal and use of features that are relevant to the indirect determination of a target analyte, such as glucose. Based on the extracted features, noninvasive analyte measurements that are biased by physiological changes in tissue may be compensated. Alternatively, the target analyte is measured indirectly based on the natural response of tissue to variations in analyte concentration.

Changes in tissue properties are reflected in key variables or features of the instrument response of any of a number noninvasive technologies, and are used to correct a biased direct analyte measurement and/or to measure the analyte indirectly in a noninvasive manner. The tissue properties themselves are responsive to and reflect physiological variations in the tissue related to variations in the concentration of analyte.

Changes in the distribution of water among tissue compartments and other physiological conditions lead to complex alterations in the measured analytical signal. These dynamic changes lead to a biased analyte measurement and have limited the state of the technology. This invention utilizes tissue properties as reflected in key features of the analytical signal to improve the accuracy and precision of the noninvasive analyte measurement.

DETAILED DESCRIPTION

Figure 2:
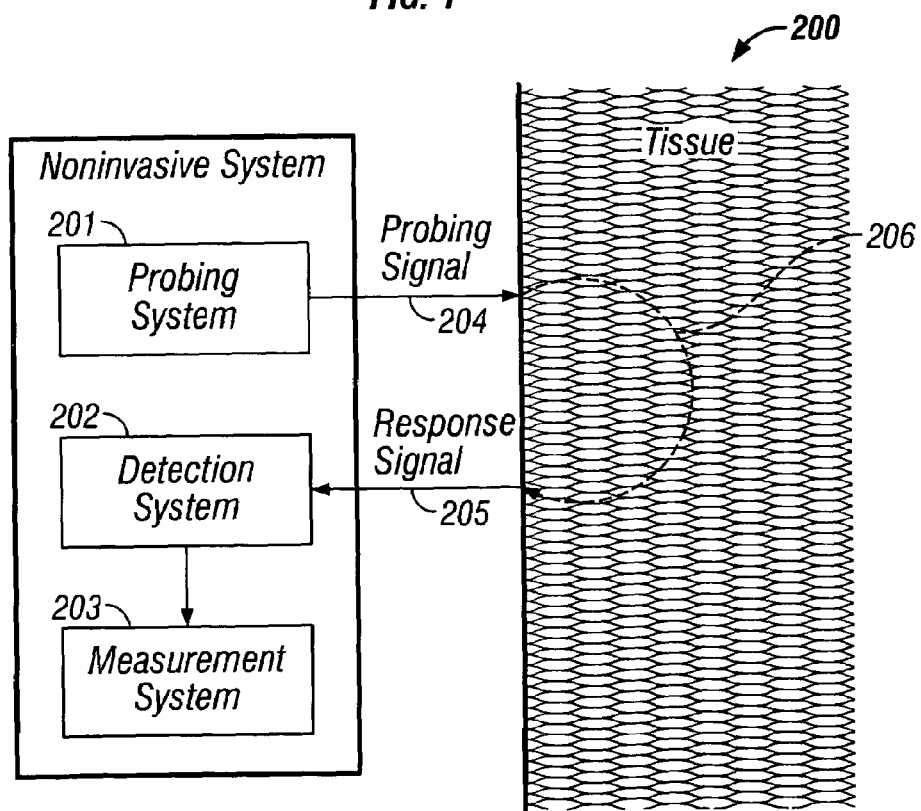
FIG. 2 provides a generalized block diagram of a noninvasive system according to the invention.

Noninvasive analyte measurement refers to the determination of the concentration or relative concentration of an analyte in the body without the extraction of a fluid or tissue sample from the body. As shown in FIG. 2, measurement begins with the application of a probing or an excitation signal 204 to a given location on the body or the use of an emission signal internally generated by the body. After interacting with the tissue containing the target analyte, the modified excitation signal 205 is detected by means of a detection system 202. The modification of the excitation signal that is unique to its interaction with the target analyte is typically used to make a determination or estimate of the concentration of the analyte through a calibration. The calibration includes a mathematical model and a system of signal processing that relate the detected signal to the target analyte.

An inherent limitation of this method is that trace analytes, such as glucose, are present in very small amounts (e.g., the concentration of glucose is typically between 2–20 mM in persons with diabetes) relative to interfering substances, such as water, protein and triglycerides or fat. In addition, the effect of a trace element on the excitation signal of a non-invasive technology such as near-infrared spectroscopy is typically minute compared to the dominant effect of background variation. These background variations are changes in the properties and characteristics of the sampled tissue and include, for example, changes in any of the following:

tissue absorption and scattering;
concentration of interfering analytes;
relative composition of interfering analytes;
distribution of water among the various compartments;
temperature;
electrical impedance;
optical rotation;
fluorescence;
mechanical strength;
elasticity;
density;
hydration;
thickness;
optical density;
refractive index of various components; and
hydration.

Calibrating a sensor directly to the effect of a trace analyte on a given excitation signal requires the extraction and discrimination of the net analyte signal from the interfering background. As a result, noninvasive measurement of trace analytes, such as glucose, on the basis of the modification by or the effect of glucose on a given excitation is extraordinarily challenging.

In addition to the acute interference described previously, long-term variations in tissue characteristics spanning periods longer than, for example, one day, pose an additional challenge since their effects could be large enough to obscure the small analyte signal. However, while the effect of analytes, such as glucose, on a given probing or excitation signal is small, often a change in the analyte concentration is accompanied by an ancillary physiological, physical or chemical response that is relatively large. A key finding related to the noninvasive measurement of glucose is that a major physiological response accompanies changes in glucose and can be detected noninvasively through the resulting changes in tissue properties. Specifically, a water shift occurs due to changes in blood glucose concentration, resulting in a redistribution of water among the intravascular, extravascular, intracellular, and extracellular compartments. This redistribution of water causes changes in the properties of skin, such as thickness or scattering, that lead to significant changes in the detected signal. While not due directly to the interaction of the excitation or probing signal with glucose, this change in the excitation signal has proven extremely useful for building and applying robust, accurate, and precise calibration models for glucose measurement.

For example, in the case of near-infrared spectroscopy, the physiological variation related to a change in glucose causes a change in the refractive index (and thus the scattering coefficient) and a change in the absorption coefficient of the various compartments and layers in tissue. As a result, the depth to which light penetrates the tissue is changed. In the case of a diffuse reflectance measurement, the changes in the absorption and scattering properties affect the amount of light diffusely reflected from a certain depth in the tissue that reaches the detector. Thus, changes in the water content in the dermis, as well as the relative water concentration in the dermal intra-cellular and extra-cellular compartments, influence the amount of light reaching the detector that has probed the subcutaneous tissue; thereby also changing the total amount of light that is absorbed by fat. In other words, changes in the fluid distribution change the magnitude and shape of the fat absorbance signal detected. The invention described herein is based upon this discovery.

In recognition of the above discovery, the invention provides a method and system for noninvasive analyte determination that uses changes in the properties of tissue related to physiological, physical, and chemical changes, such as the water distribution among various compartments, for determining conditions that are not conducive to noninvasive measurement of analytes such as glucose, and for correcting an analyte measurement on the basis of detected changes in tissue optical properties; and/or measuring the analyte indirectly on the basis of features and signals reflecting the detected properties.

The following is a detailed description of the invention directed specifically toward the noninvasive measurement of glucose. However, one skilled in the art will recognize that the method is applicable to other analytes that are both present and vary within the tissue.

The Non-Invasive System

The non-invasive system, shown in FIG. 2, utilizes an excitation or probing signal 204 to sample or probe a volume of tissue 206 in the body. A suitable location on the body for measurement may be found on the fingers, palmar region, hand, forearm, upper arm, eye, leg, plantar region, feet, toes, abdomen, earlobe, or torso although other positions are possible. The probing signal is unique to specific technologies and can be, for example, near-infrared light, electromagnetic radiation, visible light, heat, an electrical current, a radio wave, or ultrasound. While FIG. 2 depicts the probing signal 204 originating in the sensor 200, in an alternate embodiment, the probing signal can originate either from a different source not connected to the sensor or from within the body itself. The probing signal interacts with the tissue and a portion of the modified probing signal is detected by the sensor. The tissue volume 206 that is "sampled" is the portion of probed tissue from which the modified probing signal, or response signal 205, is detected by the sensor 200.

The detection system 202 detects a portion of the modified probing signal and ultimately converts the detected signal, referred to as the "tissue measurement", $m \in \Re^{1 \times N}$ where N corresponds to the dimensionality of the measurement, into a digitized form for analysis in the measurement system 203. For example, in the case of near-infrared spectroscopy, m refers to the intensity spectrum of the tissue sample represented by the intensity at N wavelengths (or wavelength ranges or selected wavelengths) selected from the 700–2500 nm wavelength range.

Figure 1:
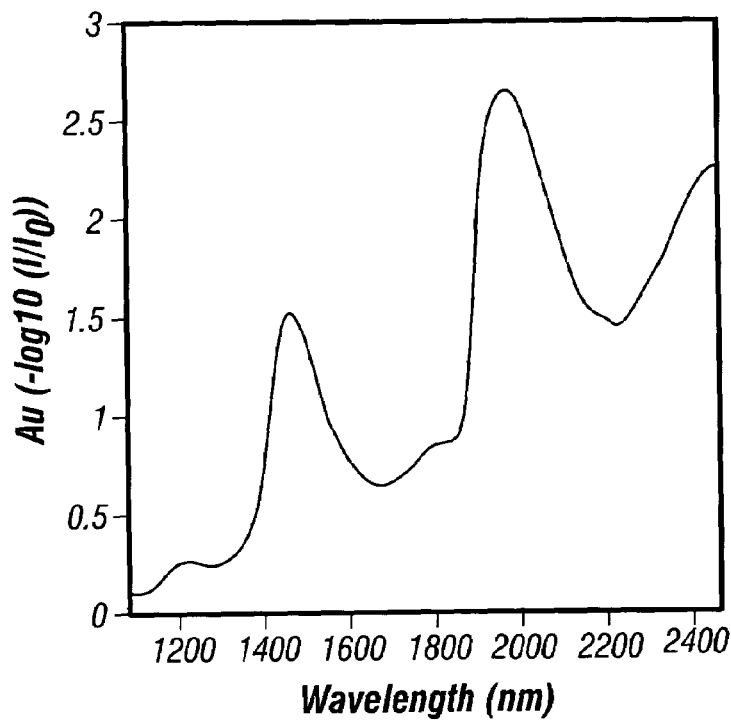
FIG. 1 provides a typical near-infrared tissue absorbance spectrum.

In the preferred embodiment of the invention, a background or reference, $m_o$, may be used to standardize or normalize the tissue measurement. Typically, the reference is collected either simultaneously with the in vivo measurement, m, or within a close time interval. The reference is a representation of the probing signal 204 applied to the tissue and is used to determine the nature and extent of the modification of the probing signal that occurs due to the interaction of the probing signal 204 and the sampled tissue volume 206. In addition, $m_o$ is used to standardize m against instrument related variation. Typically, m and $m_o$ are either ratio-ed or subtracted. For example, in the case of near-infrared spectroscopy, the absorbance of light by the sampled tissue volume is estimated according to the calculation:

$$A = -\log_{10}\left(\frac{m}{m_0}\right) \quad (3)$$

where $m_o$ is an estimate of light incident on the sample, m is an intensity spectrum of light detected and A represents an absorbance spectrum containing quantitative information that is based on the known interaction of the incident light with components of the body tissue. A plot of A versus wavelength is shown in FIG. 1, and includes absorption bands primarily due to water, fat, and protein. More particularly, however, the measurement can consist of a specific set of wavelengths in the near infrared region that have been optimized for the extraction of features and for the measurement requirements. For example, the non-invasive measurement of glucose has been found to be optimally performed in the wavelength range 1100 to 1935 nm, or a selected subset thereof such as 1150 to 1850 nm.

Alternatively, m can be referenced to a representation of the tissue measurement at some point in time prior to the collection of m and can be determined from a single tissue measurement or from the mean or a robust estimate of the mean (e.g., the trimmed mean) of several tissue measurements. Finally, m may include either a single tissue measurement collected with an instrument or a combination of several (optimally) selected tissue measurements collected over a defined measurement period and averaged. Methods for selecting the tissue measurement, used to produce the lowest noise measurement, include similarity or distance measures (i.e., select the most similar) or clustering operations.

In an alternate arrangement, the system 200, or a portion thereof, is implanted, and the measurement is made directly on soft tissue, muscle, blood vessels or skin tissue within the body. In this configuration, the measurement is performed in a manner that is non-invasive to the probed tissue although the system or a portion of the system is implanted within the body. For example, the peritoneal cavity is a suitable location for implantation and at least the probing signal source 201 and detection system 202 are implanted. However, the actual tissue probed 206 remains undisturbed by the noninvasive components. In one embodiment, telemetry is employed to transfer data or actual analyte readings to a measurement system 203 at a remote location outside the body. Alternately, a transcutaneous connector is employed. After transfer, the data or analyte measurement are processed and displayed to the user or heath care provider.

Several different embodiments of the implanted system are provided herein. The first, a consumer version, is used for incremental or continuous applications requiring intensive analysis of body analytes (e.g., glucose). A particularly useful application is nocturnal monitoring of glucose and detection or prediction of hypoglycemic events. In the second, the system is employed in a health care facility and the analyte is monitored via a computer or health care provider. A third version utilizes the system to assist in the diagnosis of diabetes, impaired glucose tolerance, or hyperinsulinemia. A fourth embodiment of the implanted system is for use in a closed-loop insulin delivery system. In this embodiment the system is a sub-component of an artificial pancreas and is used to monitor glucose levels for insulin dosage determination via an insulin pump.

As indicated above, a tissue measurement, m is passed from the detection system 202 to a measurement system 203. The measurement system 203 constitutes a processing device embodying the measurement process depicted in FIG. 3. It will be understood that the processing device of the current invention may constitute a computer system or similar electronic computing device that manipulates and transforms data represented as physical (electrical) quantities within the computer system's registers and memories into other data similarly represented as physical quantities within the computer system memories or registers, or other such information storage, transmission or display devices. Furthermore, the processing device may constitute a microprocessor, microcontroller or other processing device incorporated into an apparatus specifically constructed for the purposes of the invention. Alternately, the invention may include one or more logic devices specifically configured or programmed to perform the steps of the invented method.

Figure 3:
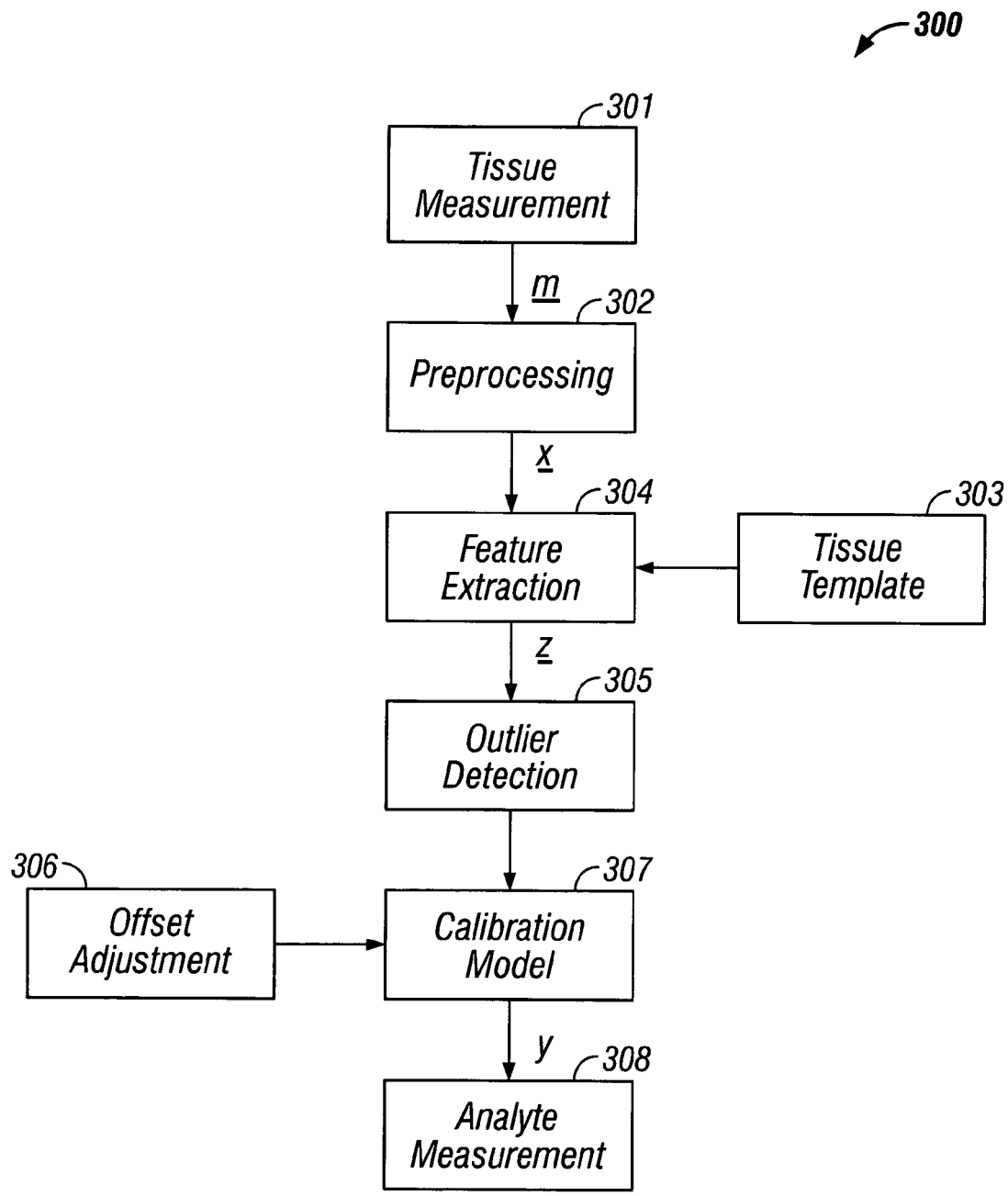
FIG. 3 provides a block diagram of a measurement process performed using the noninvasive system of FIG. 2 according to the invention.

The process shown in FIG. 3 is embodied as computer-readable code stored in a computer readable storage medium such as, but not limited to: any type of disk medium, both fixed and removable, read-only memories (ROM's) including EPROM and EEPROM, random access memories (RAM's), magnetic or optical cards, or any type of medium suitable for storing electronic instructions and data.

Referring now to FIG. 3 specifically, shown is a block diagram of a method 300 for indirect measurement of analytes through tissue properties. As described above, a noninvasive tissue measurement, m is received from the detection system 202.

Preprocessing

The tissue measurement 301, m optionally undergoes a preprocessing step 302 to enhance the analytical signal and attenuate noise. Preprocessing comprises any of such techniques as:

referencing;
converting to absorbance;
filtering;
normalizing;
wavelength selection;
or performing a translation operation.

Many other common techniques of preprocessing that are consistent with the spirit and scope of the invention are known to those skilled in the art. The choice of preprocessing techniques is dependent at least in part on the source of the analytical signal. Following preprocessing, a preprocessed tissue measurement, x is passed to the next step. If pre-processing has been omitted, the unprocessed tissue measurement m is passed to the next step. In FIG. 3, the tissue template 303, outlier detection 305, and offset adjustment 306 elements are also optional.

Feature Extraction

Feature extraction 304 is any mathematical transformation that enhances a quality or aspect of the sample measurement for interpretation [see R. Duda, P. Hart, *Pattern Classification and Scene Analysis*, John Wiley and Sons, New York (1973)]. The general purpose of feature extraction is to concisely represent or enhance any of the structural, chemical physiological, and optical properties of the tissue measurement site that are indirectly related to the target analyte. For the purposes of the invention, a set of features is developed that is indicative of the effect of the target analyte on the probed tissue. The set of features represents or reflects tissue properties or characteristics that change in various ways according to changes in the any of the structural, chemical, physical, and physiological state of the tissue. The changes in tissue state, in turn, are themselves indirectly related to the target analyte. In contrast, current practice is to directly target the signal due to glucose represented in the tissue measurement. In this context, a direct measurement is defined as a measurement based on the signal generated by the analyte during the measurement process.

An indirect measurement is based upon a physical or chemical property or characteristic that is correlated to the target analyte; but in the indirect measurement the analyte is not the direct source of the measured signal. For example, a direct glucose determination may be based upon any of the glucose absorbance bands at approximately 1590, 1730, 2150, and 2272 nm. The glucose absorbance bands are due to C—H and O—H bonds. An indirect glucose determination may be based upon the water absorbance bands centered at approximately 1450, 1900, or 2600 nm. Similarly, an indirect measurement may be based upon absorbance bands centered at approximately 1675, 1715, 1760, 2130, 2250, or 2320 nm for fat or approximately 1180, 1280, 1690, 1730, 2170, or 2285 nm for protein. Another form of indirect measurement would be based upon scattering of light. In the example of noninvasive measurement of glucose through near-infrared spectroscopy, current approaches use the absorption of light due to the glucose molecules present in the sampled tissue volume to make a glucose determination. Conventionally, then, feature extraction is based on the absorbance due to glucose that can be uniquely identified from the background interference. As previously described, isolation of a signal corresponding to an analyte that is present with relatively small absorbances, such as glucose, presents formidable challenges.

In the context of the present invention, an analysis is considered to be "direct" if the analyte of interest is probed directly or if the analyte of interest is involved in a chemical reaction that is subsequently probed. For example, in the common glucose oxidase based analysis of glucose, glucose reacts with oxygen in the presence of glucose oxidase to form hydrogen peroxide and gluconolactone. The reaction products may be involved in subsequent reactions. For example, hydrogen peroxide may be oxidized in the presence of platinum to form oxygen, $H^+$, and current. The measurement of any reaction component (glucose or oxygen) or product (gluconolactone or hydrogen peroxide) is herein defined as a direct measurement of glucose. Similarly, analysis of subsequent reactions of product such as hydrogen peroxide to current, $H^+$, or oxygen is herein termed a direct measurement.

Furthermore, a direct reading of glucose may also entail any reading in which the electromagnetic signal generated is due to interaction with glucose or a compound of glucose. For example, in a fluorescence-based glucose analyzer produced by SENSORS FOR MEDICINE & SCIENCE, INC. (Germantown Md.), glucose reversibly binds to an indicator molecule and the resulting molecule is probed by fluorescence: a "direct measurement" as defined herein. [See A. Colvin, *Optical-based sensing devices especially for in-situ sensing in humans*, U.S. Pat. No. 6,304,766, (Oct. 16, 2001); and A. Colvin, G. Dale, Gregory, S. Zerwekh, J. Lesho, R. Lynn, Optical-based sensing devices, U.S. Pat. No. 6,330,464 (Dec. 11, 2001); and A. Colvin, Arthur E.; G. Daniloff, A. Kalivretenos, D. Parker, E. Ullman, A. Nikolaitchik, *Detection of analytes by fluorescent lanthanide metal chelate complexes containing substituted ligands*, U.S. Pat. No. 6,344,360 (Feb. 5, 2002); and J. Lesho, *Implanted sensor processing system and method for processing implanted sensor output*, U.S. Pat. No. 6,400,974 (Jun. 4, 2002).]

An "indirect" method of measuring glucose involves the utilization of factors that are affected by the concentration of glucose, such as the fluid distribution in the various tissue compartments. Other terms for an "indirect" reading of this nature include physiologically correlated, correlated response, secondary response, secondary mechanism, glucose induced response, or analyte induced tissue response.

The invention advances the state of current technology through extraction of features that represent changes in the state (physical, chemical and physiological properties or characteristics) of the tissue from a prior state, distinct from the target analyte, in response to changes in the concentration of a target analyte, that occur as represented in the measured changes in tissue properties. For example, a change in glucose concentration triggers a redistribution of fluids between extra-cellular, intra-cellular, extra-vascular, and intra-vascular compartments. The features targeted for extraction, therefore, represent tissue properties related to 1) the concentration of water in each of the compartments, 2) the relative concentration of water in the compartments, 3) the size of the various compartments, 4) the change in electrical impedance resulting from the redistribution of water, and 5) the change in radiation emanating from the tissue.

Subsequently, the features are then applied to identify conditions unsuitable for analyte measurement and/or to perform an actual measurement of a tissue analyte. For example, in the case of noninvasive measurement of glucose through near-infrared spectroscopy, a resolved estimate of the magnitude of the fat band absorbance can be used to infer specific information about the dermis. Although fat is relatively absent from the dermis, near infrared radiation must propagate through the dermis to penetrate the adipose tissue beneath. Thus, physiological changes lead to corresponding changes in the optical properties of the dermis that influence the level of near-infrared radiation that penetrates to and is absorbed by the fat in adipose tissue. Therefore, the magnitude of the fat band present in a near-infrared absorbance spectrum varies, in part, according to the variation in the optical properties of the dermis. For example, as the water concentration in the dermis increases, the detected magnitude of the fat band naturally decreases and vice versa.

Several types of features are determined and optionally used in the remaining steps of the invention:

- outlier detection 305; [see T. Ruchti, C. Briggs, T. Blank. A. Lorenz, M. Mattu, M. Makarewicz, *An intelligent system for detecting errors and determining failure modes in noninvasive measurement of blood and tissue analytes*, U.S. patent application Ser. No. 10/211,478, (Aug. 1, 2002), the entirety of which is hereby incorporated by reference.]
- compensation for changes in the properties of tissue 303, 306; and
- analyte measurement 308.

Given the tissue measurement, m (or the preprocessed measurement, x):

- "simple" features are derived directly from the tissue measurement;
- additional (derived) features are determined from the simple features through one or more mathematical transformation such as addition, subtraction, division, and multiplication; and
- abstract features are derived through linear and nonlinear transformations of the tissue measurement.

While simple and derived features generally have a physical interpretation related to the properties of the tissue, such as the magnitude of the fat absorbance, the set of abstract features does not necessarily have a specific interpretation related to the physical system. For example, the scores of a factor analysis, principal component analysis, or partial-least squares decomposition are used as features, although their physical interpretation is not always known. The utility of the principal component analysis is related to the nature of the tissue measurement. The most significant variation in the tissue measurement is not caused directly by glucose but is related to the state, structure, and composition of the measurement site. This variation is modeled by the primary principal components. Therefore, the leading principal components tend to represent variation related to the structural properties and physiological state of the tissue measurement site and, consequently, reflect the tissue properties.

In certain instances, the entire tissue measurement, after suitable preprocessing, is selected within the measurement module for application of a calibration model 307 to estimate the concentration 308 of an analyte.

Tissue Template 303

Long-term fluid compartment balances are influenced by fluid intake, exercise, diet, drug therapy, and other physiological factors. The ancillary calibration of glucose to fluid compartment shifts is possible over short-term periods. The calibration of glucose to fluid shifts as reflected in tissue properties over longer periods of time may require a bias correction of the analytical signal and the associated blood glucose, in order to compensate for the sources of long-term fluid compartment shifts. One will note that Fick's Law (equation 2, supra) relates the flux in water concentration to the change in glucose concentration. Thus, this measurement based on first principles permits the determination of the relative movement of glucose. Bias correction of both the independent variable (the instrument response) and the associated glucose concentration may be utilized to enhance measurement accuracy because the initial water concentration is not strictly a function of the associated glucose concentration. An offset may be observed using Fick's Law. It may be beneficial to tie the glucose changes to a fixed point with a simple offset correction from an associated reference glucose concentration or a model designed to determine the offset to adjust the bias in the ancillary fluid shift signal.

Therefore, a background subtraction step may follow the optional preprocessing steps defined above through the determination of the difference between the estimated tissue measurement background or tissue template 303 and the extracted features, x, through:

$$z = x - (cx_t + d) \quad (4)$$

where x is the preprocessed tissue measurement or the selected set of features, $x_t$ is the estimated background or tissue template 303 associated with the measurement period, and c and d are slope and intercept adjustments to the tissue template 303. During each measurement period, the tissue template is determined through one or more tissue measurements and a data selection criterion (e.g., for example, by selecting only tissue measurements that resemble each other closely and averaging them). The measurement period is the time period over which the accuracy of the noninvasive analyte measurement remains within the desired specifications. In the preferred embodiment, $x_t$ includes features extracted from a tissue measurement collected on tissue at the beginning of the measurement period and c=1 and d=0. This process is referred to as "re-calibration" and involves both the collection of one or more tissue measurements that are processed to form a tissue template as well as an associated set of reference analyte values. The analyte values are combined according to the same strategy as that used to create the tissue template to form a measurement bias adjustment, described in greater detail below. However, the tissue template can also be any set of features from a given patient or calibration set that future tissue measurements will be compared with. In this latter embodiment, the variables c and d are determined through a least-squares fit (to minimize the Euclidean norm of z) of the tissue template over a particular wavelength range to the measured spectrum.

The tissue template is applied for the purpose of outlier detection in other measurements through distance metrics and similarity measures. In the preferred embodiment Mahalanobis distance is calculated between each tissue template and each measurement. Measurements with a distance exceeding a preset limit based upon the calibration set are rejected as invalid measurements.

Analyte Measurement

The measurement of an analyte 308 is accomplished through the application of a calibration model 307 to the processed tissue measurement, x (or m) and/or the extracted features, z. The model is determined from a calibration set of exemplary paired data points each including a preprocessed tissue measurement (x) and an associated reference analyte value (y) determined from an analysis of a blood or interstitial fluid sample. According to this process, blood, serum, plasma, or interstitial draws are taken from a tissue site that is either near the sensor sample site or has been designed/determined to reflect the sample site. For example, when non-invasive near-infrared measurements for the purpose of glucose measurement are taken for calibration on the forearm, it is possible in some individuals to collect a capillary blood draw from the same forearm or an alternate site such as opposite forearm. Alternately, rather than using blood draws, it is beneficial in some instances to use interstitial glucose values rather than capillary glucose values.

In the following discussion, analyte measurement is described as it relates to measurement of glucose. However, the description is meant to be illustrative only, and is not intended to limit the scope of the invention. In actual fact, the principles of the invention are readily applied to detection of other analytes including, but not limited to: water, protein, fat and/or lipids, blood urea nitrogen (BUN), both therapeutic and illicit drugs, and alcohol.

The calibration set is based on one or more subjects and generally contains glucose concentrations that 1) represent the expected range of glucose variation, and 2) that include spectral variation representative of that likely to be encountered in future spectral measurements. The calibration model includes an equation, a set of parameters, and corresponding computer code that is implemented to measure the subject's glucose level on the basis of the preprocessed spectral measurement. In the preferred embodiment, preprocessing 302 and feature extraction 304, together with the model 307, efficiently extract the net analyte signal of glucose where net analyte signal is the portion of the spectral signal related to the target analyte that is orthogonal to the interference [see A. Lorber, K. Faber, B. Kowalski, *Net Analyte Signal Calculation in Multivariate Calibration*, Anal. Chem, 69, pp. 1620–1626 (1997)]. The net analyte signal is then scaled and bias corrected to match the desired units of glucose measurement (e.g. mg/dL).

Several embodiments of the invention are disclosed under two categories:

In the first measurement category, the extracted features are supplemental and are applied to compensate another model for variation in the tissue properties related to changes in the effective sampled tissue volume, but which changes are unrelated to effect of glucose on the probing signal. This is accomplished by using the features that reflect the changes in tissue properties related to a water shift between compartments (or other physiological transient condition) to supplement a calibration that is based on the direct effect of glucose on the probing signal.

In the second measurement category, the extracted features related to the physical, physiological and chemical response or state of the body are primary and are used to measure the subject's glucose level indirectly. The method is based on the natural response to changes in blood glucose levels, which result in the alteration of fluid distribution in the interstitial, vascular, and cellular compartments. Such alteration of fluid distribution causes changes in the properties of tissue, as discussed previously, that are detectable through a variety of non-invasive technologies and which serve as a basis for an indirect blood glucose measurement. For example, in the case of near-infrared spectroscopy, the signal reflects the changes in the scattering and absorbance properties from different layers in skin that coincide with changes in glucose concentration. Thus, the changes in fluid distribution lead to changes in the apparent absorption of key constituents, such as fat, protein, and water, which provide a signal that is substantially higher than that of glucose and which can be used as markers for measuring glucose noninvasively. However, long-term fluid compartment balances are influenced by many factors including: fluid intake, exercise, diet, drug therapy and other physiological factors.

As noted above, indirect calibration of glucose to the ancillary fluid compartment variation is possible over short term periods while the calibration of glucose to fluid shifts over longer periods of time often requires a bias correction of the tissue measurement or analytical signal and the associated blood glucose value to compensate for the sources of long term fluid compartment shifts. Thus, this measurement only permits the determination of the movement of glucose relative to an initial point in time; and bias correction of both the tissue measurement and the associated glucose concentration to this point is required because the initial water concentration is not strictly a function of the associated glucose concentration. Therefore, in this embodiment of the invention, there is provided a method that measures the change in the properties of tissue as reflected in key constituents and a method for determining the glucose concentration on the basis of these properties.

Supplemental measurement of glucose through features is performed either through the classification system previously disclosed [see Malin et al., supra] or by supplementing the glucose measurement model with the selected features through the general equation:

$$\hat{y} = f(x_p, z) + b; \quad (5)$$

where $\hat{y}$ is the estimated glucose concentration, $x_p \in \Re^N$ is a processed tissue measurement, $z \in \Re^M$ is the set of features representative of the physiological state or properties of the tissue, $f: \Re^{N,M} \to \Re^1$ is a model used to measure glucose on the basis of the preprocessed tissue measurement and extracted features, and b is a baseline adjustment for the glucose measurement associated with both the tissue template and calibration model. The model $f(\cdot)$ is determined through a calibration set that includes tissue measurements, extracted features and reference glucose values (from blood or interstitial measurements). Designing the structure of $f(\cdot)$ is through the process of system of identification [L. Ljung, *Systems Identification: Theory for the User*, 2d.ed, Prentice Hall (1999)]. The model parameters are calculated using known methods including multivariate regression or weighted multivariate regression [N. Draper, H. Smith, *Applied Regression Analysis*, 2d.ed., John Wiley and Sons, New York (1981)], principal component regression [H. Martens, T. Naes, *Multivariate Calibration*, John Wiley and Sons, New York (1989)], partial least squares regression [P. Geladi, B. Kowalski, *Partial least-squares regression: a tutorial*, Analytica Chimica Acta, 185, pp. 1–17, (1986)], or artificial neural networks [S. Haykin, *Neural Networks: A Comprehensive Foundation*, Prentice Hall, Upper Saddle River N.J. (1994)].

In the case in which $x_p$ and z are independent, the general equation can be reduced to:

$$\hat{y} = f(x_p) - (m_s g(z) + m_i) + b; \quad (6)$$

where $f: \Re^N \to \Re^1$ is a model used to measure glucose in the absence of physiological or other tissue variation, $g: \Re^M \to \Re^1$ is a model used to map the features to a variable correlated to the error in glucose measurement caused by a change in the optical properties of the tissue, and $m_s$ and $m_i$ are slope and intercepts used to convert g(z) to the correct units. In this case, it is possible to determine $f(\cdot)$ and $g(\cdot)$ separately through an experimental design. First, $f(\cdot)$ is found through an experiment in which the tissue properties remain stable or constant while the glucose is manipulated. Second, the properties of tissue are allowed to fluctuate and $g(\cdot)$, $m_s$ and $m_i$ are determined on the basis of the error in glucose measurement where the target value for $g(\cdot)$ is given by:

$$r = y - f(x_p) - b; \quad (7)$$

where y is the reference glucose concentration. In the third embodiment, when $f(\cdot)$ and $g(\cdot)$ are determined to be linear over the range of measurement, equation #6 reduces to:

$$\hat{y} = x_p F - (m_s z G + m_i) + b; \quad (8)$$

where $F \in \Re^{N \times 1}$ and $G \in \Re^{M \times 1}$. In this embodiment, F and G are determined separately as described above using linear methods of calibration. This final realization of the supplemental use of features for glucose measurement is the preferred method.

In the second category of measurement, the extracted features are used to indirectly measure glucose through:

$$\hat{y} = (m_s g(z) + m_i) + b; \quad (9)$$

where g: $\Re^M \to \Re^1$ is a model used to map the features to a variable correlated to the reference glucose level and $m_s$ and $m_i$ are slope and intercepts used to convert g(z) to the correct units. Determination of $g(\cdot)$ is through an exemplary set (calibration set) of tissue measurements, extracted features and reference glucose concentrations (from blood or interstitial measurements). A sub-set of features is selected based on their combined correlation to the reference glucose concentration. While a priori knowledge and trial-and-error can be employed for variable selection, standard methods also exist for variable selection including: stepwise regression [Draper, et al., supra] random search techniques, genetic algorithms [D. Goldberg, *Genetic Algorithm in Search, Optimization and Machine Learning*, Addison Wesley Publishing Company (1989)] or evolutionary programming [D. Fogel, *An introduction to simulated evolutionary optimization*, IEEE Trans. On Neural Networks, 5:1 (January 1994)]. The model $g(\cdot)$ is determined through standard methods of linear or nonlinear calibration. In the linear case, $$\hat{y} = (m_s z G + m_i) + b; \quad (10)$$

where $G \in \Re^{M \times 1}$.

In the preferred embodiment of the invention, abstract features that reflect the changes in the properties of skin tissue, such as the scores from a principal components analysis or partial-least squares decomposition, are used as the independent variables for noninvasive calibration and measurement of glucose. In this embodiment, the spectral measurement, m, is preprocessed and is followed by wavelength selection to create the preprocessed vector, x. A spectral decomposition is performed according to:

$$z = xP; \quad (11)$$

where $x \in \Re^{1 \times N}$ is the preprocessed tissue measurement, N refers to the number of variables selected for calibration, $P \in \Re^{1 \times M}$ is the set of M eigenvectors or loadings obtained from a principal components analysis of the calibration set, and $z \in \Re^{1 \times M}$ is the set of abstract features or scores used to develop a calibration model and measure glucose through Equation #12 below, or through the application of a nonlinear calibration model. As described above, the calibration model can be determined through multivariate regression, weighted multivariate regression, locally weighted regression or other standard approach. While principal component regression has been described as the method for spectral decomposition, partial least squares regression can also be applied.

When abstract feature extraction is involved, the preferred method involves preprocessing, correction to the tissue template, and application of a multivariate method, such as partial-least squares regression to develop the calibration model. Glucose is then measured through the application of the identical preprocessing steps to a tissue measurement (preprocessing and tissue template correction) to obtain the processed spectral measurement, x. The glucose measurement associated with the spectral measurement is determined according to:

$$\hat{y} = xG + b; \quad (12)$$

where $G \in \Re^{M \times 1}$ is a linear transformation, derived from partial least-squares regression, that represents both the feature extraction step and the calibration model.

In an alternate form of the second embodiment, the measurement of glucose is accomplished through utilization of a calibration set and a pattern matching system. First, a set of exemplary calibration data is established with samples consisting of both a spectral measurement, that are optionally processed and subjected to feature extraction as described previously, and an associated reference glucose concentration. The calibration set is formed by the collection of samples experimentally and/or an ongoing accumulation of samples from one or more devices. The preferred method of feature extraction, following preprocessing, is a factorial decomposition such as principal components analysis.

The measurement of glucose is performed through a pattern matching step involving comparison of the features associated with a new spectral measurement and the sample features contained in the calibration set. Generally, the pattern matching step consists of the determination of the similarity between the newly acquired sample and the samples of the calibration set by either a similarity function or a distance function. In the case of isotropic features, the Euclidean distance is applied. When this assumption is not met, Mahalanobis distance is used. Further, several other suitable measures of similarity are used that depend on the expected variation and characteristics of the features.

Finally, the glucose values of one or more calibration set samples having suitable similarity to the newly acquired sample are combined to form an estimate of glucose. When the estimate is based on multiple calibration set samples, either the mean, robust estimate of the mean or a weighted mean are used in the calculation of the final estimate.

EXAMPLE 1

Bioimpedance and Bioelectrical Response

Bioimpedance and bioelectrical response measurements have been clearly demonstrated as an effective means for quantifying the water levels in various compartments of the body [see Siconolfi, supra]. As in the earlier discussion, a bioimpedance or bioelectrical response based meter is used as the apparatus shown in FIG. 2, with the tissue measurement and selected features including intracellular and extracellular fluid levels. The tissue template and related bias measurement are taken from the first bioimpedance tissue measurement of a particular measurement period (e.g., one day). A simple model is constructed via multiple linear regression on a calibration set to relate the two features to the reference glucose concentration. Non-invasive glucose measurement is made by first collecting a tissue template (the first tissue measurement of the day) and associated bias measurement (a single reference glucose concentration determined via an analysis of a blood draw). Subsequent tissue measurements are processed according to the method of FIG. 3 to produce a non-invasive glucose measurement.

In this example, the impedance of the body directly related to the presence of glucose was not used to noninvasively measure glucose. Rather, the fluid compartment shifts as reflected in the level of intracellular and extracellular fluid levels are exploited to indirectly measure the concentration of glucose in tissue.

EXAMPLE 2

Near-Infrared Diffuse Reflectance Spectroscopy

Figure 4:
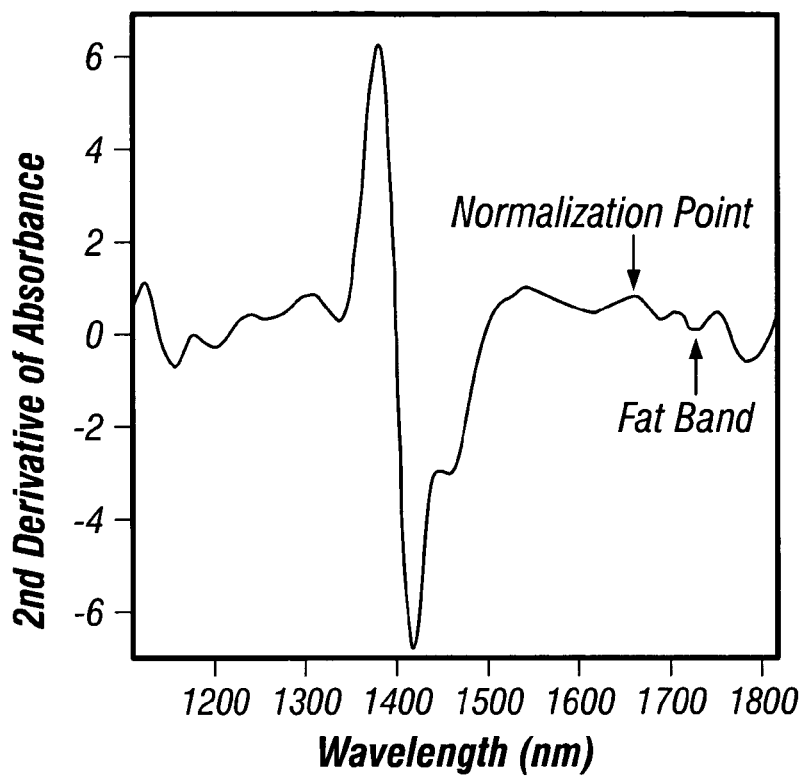
FIG. 4 provides a plot of the normalized second derivative of a spectrum of human skin.

A calibration set of paired data points was collected on a particular subject whose glucose concentration spanned the range 70–350 mg/dL. Each data point included a near-infrared absorbance spectrum of the forearm and a reference glucose concentration determined from a blood draw and analysis. The near-infrared spectra were collected using a custom built scanning near-infrared spectrometer that collected intensity spectra in diffuse reflectance over the wavelength range 1100–1950 nm. The spectral sampling interval was 1 nm and the signal-to-noise ratio at the peak intensity was approximately 90 dB. The detector used in the study was Indium-Gallium-Arsenide (InGaAs) and the optical configuration consisted of a simple fiber-optic interface to the skin with a small (<2 mm) distance between the illumination and detection fibers. Reference spectra were recorded before each sample measurement by scanning an 80% SPECTRALON reflectance material from Labsphere, Inc. (North Sutton N.H.). The absorbance spectrum was calculated as in Equation #3. The spectra were processed via the second derivative to enhance features related to absorption of water, fat, and protein. For the purpose of analysis, the fat band was selected as a feature representing one or more properties of the tissue including the 1) thickness of the dermis, 2) the scattering properties of the skin, and 3) the concentration of water in the dermis. The feature was extracted from the second derivative of the absorbance spectra, as shown in FIG. 4, and normalized to a critical point near 1650 nm through a difference calculation. Outlier detection was not performed.

Figure 5:
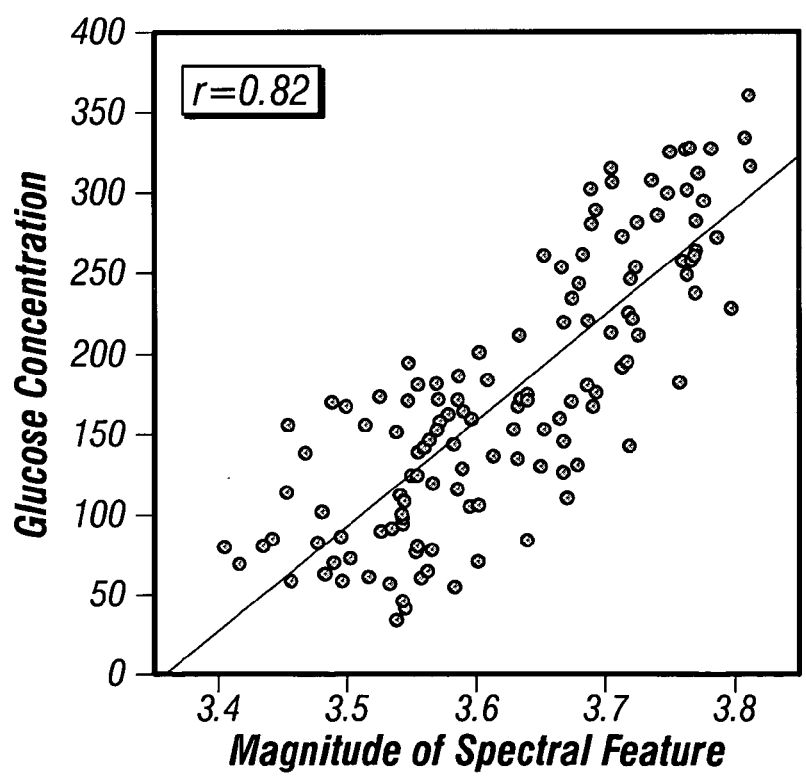
FIG. 5 provides a scatter plot of reference glucose concentrations versus the magnitude of the second derivative at 1720 nm according to the invention.

A plot of the normalized fat band versus the reference glucose concentration is given in FIG. 5. The high degree of correlation between the feature and reference glucose concentration indicates that glucose measurement based on this extracted feature is feasible. A simple linear regression is performed to determine the model parameters of the equation. To complete the system described in FIG. 3, a prior tissue measurement was selected as the tissue template 303 after processing and the reference glucose concentration taken once concurrently with the tissue template applied as the bias (offset) adjustment 306.

Although the feature described in this example clearly correlated with the concentration of glucose, it was chosen to represent the tissue properties, rather than the absorption and scattering properties of glucose. Therefore, the example demonstrates a simple means for indirectly measuring glucose through tissue variation reflected in the normalized fat band.

EXAMPLE 3

Near-Infrared Diffuse Reflectance Spectroscopy

Although the prior example demonstrated a simple system for measuring glucose indirectly, a more complex model is necessary when significant interference is present or when the calibration model must be applied to more than one individual. In a second example, a large data set of paired data points was collected on 20 individuals. The data was separated into calibration (four subjects) and test sets (16 subjects). The following preprocessing steps were used to enhance the tissue properties reflected in the absorbance spectra: 1) band-pass filtering, 2) wavelength selection, 3) multiplicative scatter correction and 4) wavelength selection.

The band-pass filtering operation was performed to remove low-frequency interference and attenuate the high frequency noise.

Wavelength selection was performed to optimize the inclusion of gross spectral features (protein, fat, and water) whose variation reflects variation in tissue properties related to a fluid shift, rather than the absorption due to glucose.

Figure 6:
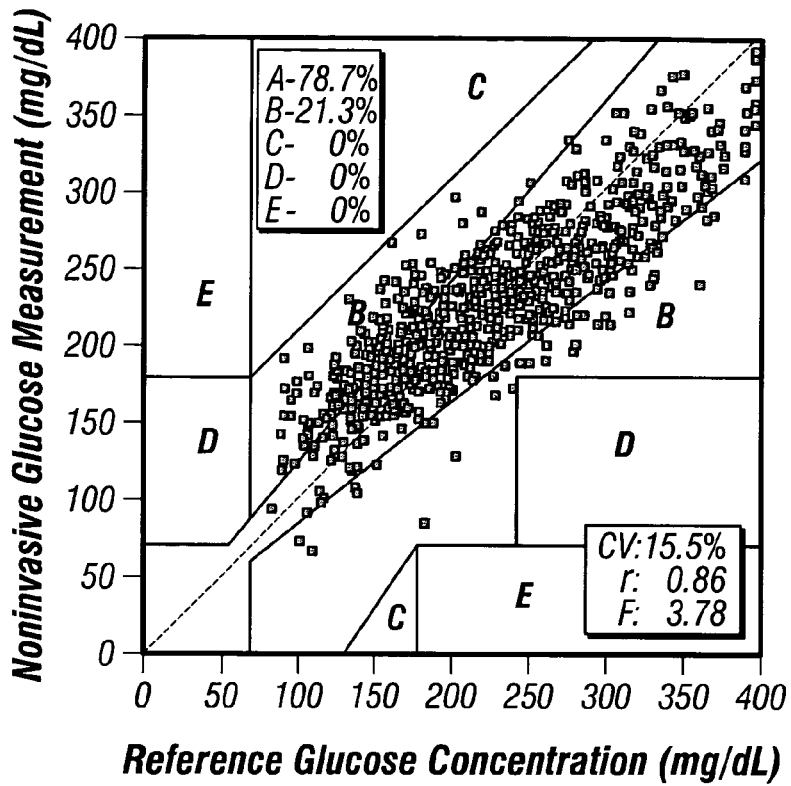
FIG. 6 provides a concentration correlation plot of measured versus reference glucose concentrations according to the invention.

A different tissue template was selected for each patient and each measurement period (one day) from a combination of the processed absorbance spectra. Application of the tissue template was followed by a principle component analysis. The abstract features of the analysis were selected as features and a multiple linear regression was performed to determine a calibration model as in Equation #12. The method of FIG. 3 was applied to the independent test set. The non-invasive glucose measurements versus the glucose measurements based on a capillary blood draw are shown in FIG. 6. The clinically acceptable results demonstrate the effectiveness of the invention and the utility of using the physiological and chemical response to glucose as an indirect measurement for noninvasive glucose measurement.

EXAMPLE 4

Tissue Scattering Coefficients

In the case of a noninvasive means for measuring the scattering properties of tissue, prior efforts have attempted to use the scattering directly related glucose as a means for measuring glucose [see J. Bruulsema, J. Hayward, T. Farrell, M. Patterson, L. Heinemann, M. Berger, M. Koschinsky, J. Sandahl-Christiansen, H. Orskov, M. Essenpreis, G. Schmelzeisen-Redeker, D. Böcker, *Correlation between blood glucose concentration in diabetics and noninvasively measured tissue optical scattering coefficient*, Optics Letters, v.22:3, pp. 190–192 (Feb. 1, 1997). Conversely, the tissue water content is labeled as a potential source of physiological interference. However, according to the invention herein described, a more suitable means for measuring glucose is based on the change in the scattering of tissue caused by fluid shifts between the various compartments, which is based on the tissue water content. Such shifts affect the size, distribution, and separation of scattering centers as well as the refractive index at each boundary. Consequently, the fluid compartment shift related to a change in glucose concentration can be detected via the gross scattering properties of the tissue. Therefore, the application of the invented method to noninvasive glucose measurement via scattering changes induced by fluid shifts and other physiological responses to glucose involves the steps shown in FIG. 3, in which the tissue measurement is the scattering change induced by a fluid shift rather than that change induced by shifts in glucose.

EXAMPLE 5

Mission Spectroscopy

The physiological response of tissue to varying glucose concentration yields a redistribution of fluid in various tissue layers and compartments, as described above. This in turn causes a slight change in the radiative emission of tissue. Hence, a set of features exists that represents the emission of water rather than glucose and which can be used as described herein to indirectly measure glucose. Using the emission properties of tissue as the tissue measurement (and associated features after suitable processing) and the first measurement of the measurement period as the tissue template, the noninvasive measurement of glucose can be accomplished through emission spectroscopy using the method of FIG. 3, wherein the probing signal in the noninvasive system may or may not exist, and may or may not be a temperature modifier. The response signal is emitted infrared radiation (near, mid, and far) generated from within the tissue.

EXAMPLE 6

Raman Spectroscopy

Raman spectroscopy has been applied to the non-invasive determination of glucose by measuring the scattered light that has been influenced by the oscillation and rotation of the glucose molecule [see Chaiken et al., supra; and S. Wang, C. Hasty, P. Watson, J. Wickstead, R. Stith and W. March, *Analysis of Metabolites in Aqueous Solutions Using Laser Raman Spectroscopy*, Applied Optics, v.32:6, pp. 925–929]. However, the large background signal due to scattering of other constituents in the body results in a challenging measurement when the scattering signal directly related to glucose is targeted for measurement. However, as described previously, the physiological response due to glucose causes an alteration of tissue properties that affects Raman scattering related to fat, protein, and the thickness, density and distribution of proteins. As glucose varies, the scattering of each of these properties varies in a manner that is manifested in the Raman spectrum. Consequently, through either the extraction of features related to the physiological response due to variations in glucose concentration or abstract feature extraction, the methodology described herein and illustrated in FIG. 3 can be applied to effectively measure glucose noninvasively via Raman Spectroscopy.

EXAMPLE 7

Near-Infrared Spectroscopy and Artificial Neural Networks

A calibration set of 1164 paired data points encompassed 70 separate experiments on 11 subjects. Each data point included a near-infrared absorbance spectrum of the forearm and a reference glucose concentration determined from analysis of a blood sample. The near-infrared spectra were collected using a custom-built scanning near-infrared spectrometer that collected intensity spectra in diffuse reflectance over a wavelength range of approximately 1100–1950 nm. The spectral sampling interval was approximately 1.6 nm and the signal-to-noise ratio at the peak intensity was approximately 90 dB. A tungsten halogen lamp, optical filters and fiber optics were used to deliver light to the skin. A detection fiber, surrounded by the illumination fibers, collected and delivered light from the skin to a spectrograph. A six hundred-element array of Indium-Gallium-Arsenide (InGaAs) and extended Indium-Gallium-Arsenide (InGaAs) detectors was used to provide a measure of the light intensity over the target wavelength range. Reference spectra were recorded before each sample measurement by scanning a 99% SPECTRALON reflectance material provided by LAB-SPHERE, INC. (North Sutton N.H.). The absorbance spectrum was calculated as in Equation #3. The spectra were smoothed and processed via the first derivative to enhance features related to absorption of water and re-sampled approximately every 30 nm. In addition, a tissue template was determined for each day and subject and was subtracted from the processed spectra.

An artificial neural network (ANN) was designed with 25 input nodes (including one bias node), two hidden layers (with eight and four neurons respectively) and an output neuron. With the exception of the input neurons, a sigmoidal activation function was used in each neuron. The calibration set was applied to parameterize (or train) the ANN through an extended Kalman filter as described by S. Singhal, L. Wu, "*Training feed-forward networks with the extended Kalman algorithm*," Proceedings of the ICASSP, pp. 1187–1190 (1989). Training was monitored with a random sampling of the calibration set and was terminated after approximately 12 iterations.

Figure 7:
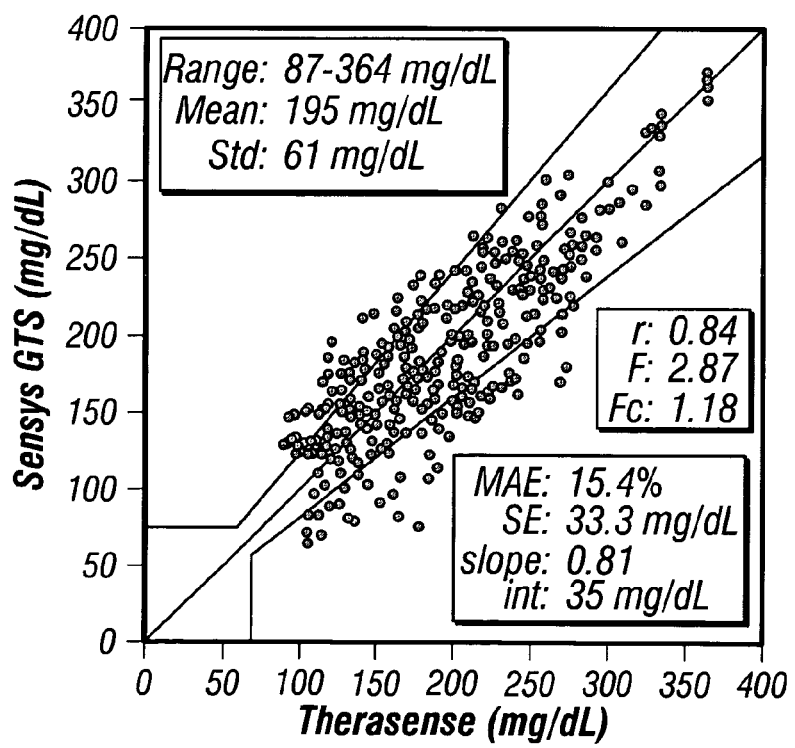
FIG. 7 provides a plot of noninvasive glucose measurements predicted by an artificial neural network versus reference glucose concentration according to the invention.

A separate set of test data was collected consisting of 416 samples. Each spectrum was processed as described above and propagated through the ANN to provide an estimate of glucose. A plot of the non-invasive glucose measurement (SENSYS GTS, Chandler Ariz.) versus the reference capillary measurement (THERASENSE, Alameda Calif.) is shown in FIG. 7 with an average absolute error of approximately 15%.

One skilled in the art will appreciate that the invention is applicable to noninvasive technologies capable of measuring a tissue property that varies according to the physiological response of tissue to glucose. Thus, the following technologies are recognized for use with the invention:

Kromoscopy (reflectance and transmission);
Near-infrared spectroscopy (700–2500 nm, any of diffuse reflectance, transflectance, and transmission);
Mid-infrared spectroscopy (4000–700 $cm^{-1}$, any of reflectance and transmission);
ATR (attenuated total reflectance);
Oscillating thermal gradient spectrometry;
Far infra-red radiation spectroscopy;
Radio wave impedance;
Polarimetry;
Infrared and FT (Fourier transform)-IR spectroscopy;
IR transmission and IR diffuse reflectance (ATR);
Fluorescence (illuminescense) spectrometry;
Raman spectroscopy;
Photoacoustic and pulse laser photoacoustic spectroscopy;
Photon scattering (400–2500 nm);
Emission spectroscopy;
Passive IR spectroscopy;
Bioelectric impedance or potentiometry, bioelectrical response spectroscopy;
Ultrasound;
Visible spectroscopy (400–700 nm);
Far infrared spectroscopy; and
Ultra violet (UV) (200–400 nm);

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

What is claimed is:

1. A method for noninvasive measurement of a target analyte in a tissue, comprising the steps of:
    collecting an analytical signal from the tissue, said collected signal comprising a tissue measurement;
    extracting at least one spectral feature from the analytical signal indicative of the effect of the target analyte on the probed tissue; and
    either correcting a direct analyte measurement based on said at least one feature; or
    calculating concentration of said analyte indirectly by application of a calibration model to said at least one feature.

2. The method of claim 1, wherein said analytical signal is generated using any of:
    fluorescence spectroscopy;
    ultraviolet spectroscopy from 200 to 400 nm;
    visible spectroscopy from 400 to 700 nm;
    infrared and Fourier transform infrared (FTIR) spectroscopy;
    passive infrared spectroscopy;
    mid infrared spectroscopy from 4000–700 cm$^{-1}$ in any of diffuse reflectance and transmission;
    attenuated total reflectance (ATR) spectroscopy;
    far infrared radiation spectroscopy;
    Kromoscopy in reflection or transmission;
    emission spectroscopy;
    Raman spectroscopy;
    photoacoustic and pulse laser photoacoustic spectroscopy;
    photon scattering from 400 to 2500 nm;
    bioelectrical response spectroscopy;
    oscillating thermal gradient spectroscopy;
    polarimetry;
    ultrasound spectroscopy;
    near infrared spectroscopy from 700 to 2500 nm in any of diffuse reflectance, transflectance, and transmission mode; and
    radio wave spectroscopy.

3. The method of claim 2, further comprising the step of: preprocessing said tissue measurement.

4. The method of claim 3, wherein said step of preprocessing said tissue measurement comprises any of the steps of:
    correcting said signal utilizing a reference;
    filtering said signal;
    calculating any of a first and second derivative of said signal;
    normalizing said signal;
    selecting portions of said signal;
    scatter correcting said signal; and
    translating said signal.

5. The method of claim 3, further comprising the step of:
    determining difference between a tissue template and either the preprocessed tissue measurement or the at least one extracted feature according to:

$z = x - (cx_t + d);$ wherein x comprises either the pre-processed measurement or a set of at least one extracted features, $x_t$ comprises a tissue template associated with a measurement period, and c and d are slope and intercept adjustments to the tissue template.

6. The method of claim 5, wherein said tissue template is determined through one or more tissue measurements combined according to a predetermined data selection criterion during each measurement period.

7. The method of claim 6, wherein a measurement period comprises a time period over which accuracy of the tissue measurement remains within desired specifications.

8. The method of claim 6, further comprising the step of:
    providing an associated set of reference values combined according to said predetermined data selection criterion to form a measurement bias adjustment.

9. The method of claim 5, wherein the tissue template comprises any set of features from a given subject or calibration set that future tissue measurements will be compared with, wherein c and d are determined through least-square fit of the tissue template over a particular wavelength range to the tissue measurement.

10. The method of claim 5, wherein the step of correcting a direct analyte measurement based on said at least one feature comprises:
    supplementing a second calibration model based on direct effect of glucose on said analytical signal with said at least one selected feature according to:

$\hat{y} = f(x_p, z) + b;$ where $\hat{y}$ is an estimated analyte concentration, $x_p \in \Re^N$ is a processed tissue measurement, $z \in \Re^M$ is a set of features representative of the physiological state or optical properties of the tissue, f: $\Re^{N,M} \to \Re^1$ is a model used to measure the analyte on the basis of a preprocessed measurement and at least one extracted feature, and b is a baseline adjustment for analyte measurement associated with both a tissue template and said second calibration model.

11. The method of claim 10, wherein measurement site comprises any of:
    a finger;
    palmar region;
    hand;
    forearm;
    upper arm;
    eye;
    earlobe;
    torso;
    abdominal region;
    leg;
    plantar region;
    a foot; and
    toes.

12. The method of claim 5, wherein the step of correcting a direct analyte measurement based on said at least one feature comprises:
    supplementing a second calibration model based on direct effect of glucose on said analytical signal with said at least one selected feature according to:

$\hat{y} = f(x_p) - (m_s g(z) + m_i) + b;$ where $\hat{y}$ is an estimated analyte concentration, $x_p \in \Re^N$ is a processed tissue measurement, $z \in \Re^M$ is a set of features representative of any of the structural, chemical, physiological and optical properties of the tissue, wherein $x_p$ and z are independent, where f: $\Re^N \to \Re^1$ is a model used to measure the analyte in the absence of physiological or other tissue variation, $g: \Re^M \to \Re^1$ is a model used to map said at least one feature to a variable correlated to error in analyte measurement caused by a change in the properties of the tissue, $m_s$ and $m_i$ are slope and intercepts used to convert $g(z)$ to correct units, and b is a baseline adjustment for analyte measurement associated with both a tissue template and said calibration model.

13. The method of claim 12, wherein $f(\cdot)$ and $g(\cdot)$ are separately determined experimentally, wherein $f(\cdot)$ is determined by manipulating analyte concentration while tissue properties remain constant, and wherein the properties of tissue are allowed to fluctuate and $g(\cdot)$, $m_s$ and $m_i$ are determined on the basis of the error in analyte measurement where target value for $g(\cdot)$ is given by:

$$r = y - f(x_p) - b;$$

where y is a reference analyte concentration.

14. The method of claim 13, wherein said step of correcting a direct analyte measurement on the basis of said detected changes comprises supplementing said second model with at least one selected features according to:

$$\hat{y} = x_p F - (m_s z G + m_i) + b;$$

wherein $f(\cdot)$ and $g(\cdot)$ are determined to be linear over range of measurement and where $F \in \Re^{N \times 1}$ and $G \in \Re^{M \times 1}$.

15. The method of claim 12, wherein said y values are determined from samples of blood, serum, plasma or interstitial fluid taken from a fingertip, a site near the measurement site or an alternate site.

16. The method of claim 5, wherein said calibration model is determined from a calibration set of exemplary paired data points each consisting of a preprocessed spectral measurement, x, and an associated reference analyte value, y.

17. The method of claim 16, wherein said step of measuring said analyte indirectly on the basis of said at least one spectral feature comprises using at least one extracted features to measure glucose indirectly according to:

$$\hat{y} = (m_s g(z) + m_i) + b;$$

where $g: \Re^M \to \Re^1$ comprises said model, said model used to map set of features z to a variable correlated to a reference glucose level and $m_s$ and $m_i$ are slope and intercepts used to convert $g(z)$ to the correct units and b is a baseline adjustment for glucose measurement.

18. The method of claim 17, wherein said at least one feature is selected based on their combined correlation to the reference analyte concentration.

19. The method of claim 18, wherein said at least one feature is selected based on any of:
a priori knowledge;
trial-and-error;
stepwise regression;
random search techniques;
genetic algorithms; and
evolutionary programming.

20. The method of claim 18, wherein $g(\cdot)$ is determined according to:

$$\hat{y} = (m_s z G + m_i) + b;$$

where $G \in \Re^{M \times 1}$.

21. The method of claim 2, wherein feature extraction comprises any mathematical transformation that enhances a quality or aspect of said tissue measurement to concisely represent tissue state, wherein tissue state comprises any of structural, chemical, physiological, and optical properties of the tissue that are indirectly related to the target analyte.

22. The method of claim 21, wherein said step of extracting at least one feature comprises the step of:
developing a set of features that represents tissue state based on distinct patterns that change according to changes in said structural, chemical, physiological and optical properties, wherein changes in tissue state are indirectly related to changes in target analyte concentration.

23. The method of claim 22, wherein said changes in tissue state comprise any of:
alteration of water distribution among body compartments;
changes to thickness of various skin layers; and
changes in distance from skin surface to adipose tissue layer.

24. The method of claim 23, wherein said changes in tissue state result in alterations of skin properties, said skin properties comprising any of:
localized scattering;
localized refractive index; and
skin thickness.

25. The method of claim 21, wherein a features includes any of:
a simple feature;
a derived features;
an abstract feature;
a normalization point;
a fat band point;
a protein band point; and
a water band point.

26. The method of claim 25, wherein said simple feature is derived directly from the tissue measurement.

27. The method of claim 25, wherein said derived feature comprises at least one mathematical combinations of simples features.

28. The method of claim 25, wherein said abstract feature is derived through at least one transformation of the analytical signal, wherein said at least one transformation is either linear or nonlinear.

29. The method of claim 2, further comprising any of the steps of:
detecting conditions not conducive to analyte measurement; and
detecting outliers.

30. The method of claim 29, wherein said step of performing outlier detection comprises:
performing Mahalanobis distance outlier detection.

31. The method of claim 1, wherein at least one abstract feature that reflects changes in tissue properties is used as independent variables for said calibration model and wherein said step of measuring said analyte indirectly comprises:
preprocessing said tissue measurement; and
decomposing said preprocessed tissue measurement according to:

$$z = xP;$$

where $x \in \Re^{1 \times N}$ is the preprocessed tissue measurement, N is number of wavelengths selected for calibration, $P \in \Re^{1 \times M}$ is a set of M eigenvectors or loadings obtained from a principal components analysis of a calibration set and $z \in \Re^{1 \times M}$ is a set of abstract features used to measure glucose through application of said calibration model, wherein said model is either linear or nonlinear.

32. The method of claim 31, wherein analyte measurement associated with the tissue measurement is determined according to:

$$\hat{y}=xG+b;$$

where $G \in \mathfrak{R}^{M \times 1}$ is a linear transformation, derived from partial least-squares regression that represents both the feature extraction step and the calibration model.

33. The method of claim 1, wherein said analyte comprises any of:
water;
fat;
protein; and
glucose.

34. The method of claim 1, wherein said step of collecting said analytical signal comprises making repeated tissue measurements at predetermined time intervals.

35. The method of claim 1, wherein said analyte is glucose.

36. The method of claim 35, wherein said calibration model uses multivariate analysis.

37. The method of claim 36, wherein said analytical signal is generated using:
near infrared spectroscopy from 700 to 2500 nm in any of diffuse reflectance, transflectance, and transmission mode.

38. The method of claim 37, further comprising steps of:
correcting said signal;
subsequently calculating a derivative of said signal; and
subsequently selecting portions of said signal.

39. A system for noninvasive measurement of a target analyte in a tissue, comprising:
means for noninvasively collecting an analytical signal from said tissue, said collected signal comprising a tissue measurement; and
means for measuring concentration of said analyte based on at least one spectral feature extracted from the analytical signal indicative of the effect of the target analyte on the probed tissue.

40. The system of claim 39, wherein said means for collecting an analytical signal comprises:
means for detecting said analytical signal; and
means for digitizing said detected analytical signal.

41. The system of claim 40, wherein said means for measuring concentration of said analyte comprises:
a processing element in communication with said collection means, wherein said collection means passes said digitized signal to said processing element; and
computer readable code embodied on a tangible medium, wherein said processor executes said code, said code comprising code means for executing a method for noninvasive measurement of said target analyte, said method comprising the steps of:
collecting an analytical signal from the tissue, said collected signal comprising a tissue measurement;
extracting at least one feature from the analytical signal indicative of the effect of the target analyte on the probed tissue; and
either correcting a direct analyte measurement based on said at least one feature; or
calculating concentration of said analyte indirectly by application of a calibration model to said at least one feature.

42. The system of claim 41, said system further comprising the step of:
preprocessing said tissue measurement.

43. The system of claim 42, wherein said step of preprocessing said tissue measurement comprises any of the steps of:
correcting said signal utilizing a reference;
filtering said signal;
calculating any of a first and second derivative of said signal;
selecting portions of said signal;
normalizing said signal;
scatter correcting said signal; and
translating said signal.

44. The system of claim 41, wherein feature extraction comprises any mathematical transformation that enhances a quality or aspect of said tissue measurement to concisely represent tissue state, wherein tissue state comprises any of structural, chemical, physiological, and optical properties of the tissue that are indirectly related to the target analyte.

45. The system of claim 44, wherein said step of extracting at least one feature comprises the step of:
developing a set of features that represents tissue state based on distinct patterns that change according to changes in said structural, chemical, physiological and optical properties, wherein changes in tissue state are indirectly related to changes in target analyte concentration.

46. The system of claim 45, wherein physiological changes comprise any of:
alteration of water distribution among body compartments;
changes to thickness of various skin layers; and
changes in distance from skin surface to adipose tissue layer.

47. The system of claim 46, wherein said physiological changes result in alterations of skin properties, said skin properties comprising any of:
localized scattering;
localized refractive index; and
skin thickness.

48. The methed system of claim 46, wherein a feature includes any of:
a simple feature;
a derived feature;
an abstract feature;
a normalization point;
a fat band point;
a protein band point; and
a water band point.

49. The system of claim 48, wherein said simple feature is derived directly from the tissue measurement.

50. The system of claim 48, wherein said derived feature comprises at least one mathematical combination of simple features.

51. The system of claim 48, wherein said abstract feature is derived through at least one transformation of the analytical signal, said at least one transformation is either linear or nonlinear.

52. The system of claim 41, said system further comprising the step of:
determining difference between a tissue template and either the preprocessed tissue measurement or the at least one extracted feature according to:

$$z=x-(cx_t+d);$$

wherein x comprises either the pre-processed measurement or a set of at least one extracted feature, $x_t$ comprises a tissue template associated with a measurement period, and c and d are slope and intercept adjustments to the tissue template.

53. The system of claim 52, wherein said tissue template is determined through one or more tissue measurements combined according to a predetermined data selection criterion during each measurement period.

54. The system of claim 53, wherein a measurement period comprises a time period over which accuracy of the tissue measurement remains within desired specifications.

55. The system of claim 53, said system further comprising the step of:
providing an associated set of reference values combined according to said predetermined data selection criterion to form a measurement bias adjustment.

56. The system of claim 53, wherein the tissue template comprises any set of features from a given subject or calibration set that future tissue measurements will be compared with, wherein c and d are determined through least-square fit of the tissue template over a particular wavelength range to the tissue measurement.

57. The system of claim 52, wherein the step of correcting a direct analyte measurement based on said at least one feature comprises:
supplementing a second calibration model based on direct effect of glucose on said analytical signal with said at least one selected feature according to:

$$\hat{y}=f(x_p,z)+b;$$

where $\hat{y}$ is an estimated analyte concentration, $x_p \in \Re^N$ is a processed tissue measurement, $z \in \Re^M$ is a set of features representative of the physiological state or optical properties of the tissue, f: $\Re^{N,M} \to \Re^1$ is a model used to measure the analyte on the basis of a preprocessed measurement and at least one extracted feature, and b is a baseline adjustment for analyte measurement associated with both a tissue template and said second calibration model.

58. The system of claim 52, wherein the step of correcting a direct analyte measurement based on said at least one feature comprises:
supplementing a second calibration model based on direct effect of glucose on said analytical signal with said at least one selected feature according to:

$$\hat{y}=f(x_p)-(m_s g(z)+m_i)+b;$$

where $\hat{y}$ is an estimated analyte concentration, $x_p \in \Re^N$ is a processed tissue measurement, $z \in \Re^M$ is a set of features representative of any of the structural, chemical, physiological and optical properties of the tissue, wherein $x_p$ and z are independent, where F: $\Re^n \to \Re^1$ is a model used to measure the analyte in the absence of physiological or other tissue variation, g: $\Re^M \to \Re^1$ is a model used to map the at least one feature to a variable correlated to error in analyte measurement caused by a change in the properties of the tissue, $m_s$ and $m_i$ are slope and intercepts used to convert g(z) to correct units, and b is a baseline adjustment for analyte measurement associated with both a tissue template and said calibration model.

59. The system of claim 58, wherein f(·) and g(·) are separately determined experimentally, wherein f(·) is determined by manipulating analyte concentration while tissue properties remain constant, and wherein the properties of tissue are allowed to fluctuate and g(·), $m_s$ and $m_i$ are determined on the basis of the error in analyte measurement where target value for g(·) is given by:

$$r=y-f(x_p)-b;$$

where y is a reference analyte concentration.

60. The system of claim 52, wherein said step of correcting a direct analyte measurement on the basis of said detected changes comprises supplementing said second model with at least one selected feature according to:

$$\hat{y}=x_p F-(m_s z G+m_i)+b;$$

wherein f(·) and g(·) are determined to be linear over range of measurement and where $F \in \Re^{N \times 1}$ and $G \in \Re^{M \times 1}$.

61. The system of claim 52, wherein said calibration model is determined from a calibration set of exemplary paired data points each consisting of a preprocessed spectral measurement, x and an associated reference analyte value, y.

62. The system of claim 52, wherein said step of measuring said analyte indirectly on the basis of at least one spectral feature comprises using at least one extracted feature to measure glucose indirectly according to:

$$\hat{y}=(m_s g(z)+m_i)+b;$$

where g: $\Re^M \to \Re^1$ comprises said model, said model used to map a set of features z to a variable correlated to a reference glucose level and $m_s$ and $m_i$ are slope and intercepts used to convert g(z) to the correct units and b is a baseline adjustment for glucose measurement.

63. The system of claim 41, said system further comprising any of the steps of:
detecting conditions not conducive to analyte measurement; and
detecting outliers.

64. The system of claim 39, wherein at least a portion of said system is implanted in body of a subject, said system adapted to measure said analyte in a manner that is noninvasive to tissue probed.

65. The system of claim 64, wherein site of implantation comprises peritoneal cavity.

66. The system of claim 64, wherein said measurement means is located remotely from said body.

67. The system of claim 66, wherein said measurement system and said collection system are in communication via telemetry.

68. The system of claim 39, further comprising means for generating a probing signal, wherein said probing signal is directed toward said tissue.

69. The system of claim 39, wherein said tissue measurement comprises an in vivo measurement from a human subject and wherein said target analyte comprises glucose.

70. The system of claim 69, wherein said analytical signal is derived from use of any of:
fluorescence spectroscopy;
ultraviolet spectroscopy from 200 to 400 nm;
visible spectroscopy from 400 to 700 nm;
infrared and Fourier transform infrared (FTIR) spectroscopy;
passive infrared spectroscopy;
mid infrared spectroscopy from 4000–700 $cm^{-1}$ in any of diffuse reflectance and transmission;
attenuated total reflectance (ATR) spectroscopy;
far infrared radiation spectroscopy;
Kromoscopy in reflection or transmission;
emission spectroscopy;
Raman spectroscopy:
photoacoustic and pulse laser photoacoustic spectroscopy;
photon scattering from 400 to 2500 nm;
bioelectrical response spectroscopy;
oscillating thermal gradient spectroscopy;
polarimetry;

ultrasound spectroscopy;
near infrared spectroscopy from 700 to 2500 nm in any of diffuse reflectance, transflectance, and transmission mode; and
radio wave spectroscopy.

71. The system of claim 69, wherein said analytical signal is derived from use of light scattering.

72. The system of claim 69, wherein said at least one feature comprises any of:
one or more water absorbance bands;
one or more fat absorbance bands; and
one or more protein absorbance bands.

73. The system of claim 72, wherein said one or more water absorbance bands are centered at any of the wavelengths:
approximately 1450 nm;
approximately 1900 nm; and
approximately 2600 nm.

74. The system of claim 73, wherein said one or more fat absorbance bands are centered at any of the wavelengths:
approximately 1675 nm;
approximately 1715 nm;
approximately 1760 nm;
approximately 2130 nm;
approximately 2250 nm; and
approximately 2320 nm.

75. The system of claim 73, wherein said one or more protein absorbance bands are centered at any of the wavelengths:
approximately 1180 nm;
approximately 1280 nm;
approximately 1690 nm;
approximately 1730 nm;
approximately 2170 nm; and
approximately 2285 nm.

76. The system of claim 39, wherein collecting said analytical signal from said tissue comprises taking repeated tissue measurements at predetermined time intervals.

77. A method for noninvasive measurement of a target analyte in a tissue, comprising the steps of:
collecting an analytical signal from the tissue, said collected signal comprising tissue measurement;
extracting at least one feature from the analytical signal indicative of the effect of the target analyte on the probed tissue, wherein said effect comprises alteration of water distribution among body compartments; and
either correcting a direct analyte measurement based on said at least one feature; or
calculating concentration of said analyte indirectly by application of a calibration model to said at least one feature.

78. The method of claim 77, further comprising the step of:
preprocessing said tissue measurement.

79. The method of claim 77, further comprising any of the steps of:
detecting conditions not conducive to analyte measurement; and
detecting outliers.

80. The method of claim 77, wherein said analyte comprises any of:
water;
fat;
protein; and
glucose.

81. The system of claim 77, wherein said at least one feature comprises any of:
one or more water absorbance bands;
one or more fat absorbance bands; and
one or more protein absorbance bands.

82. A method for noninvasive measurement of a target analyte in a tissue, comprising the steps of:
collecting an analytical signal from the tissue, said collected signal comprising a tissue measurement;
extracting at least one feature from the analytical signal indicative of the effect of the target analyte on the probed tissue wherein said at least one feature comprises at least a portion of a water band, a portion of a fat band, and a portion of a protein band;
either correcting a direct analyte measurement based on said at least one feature; or
calculating concentration of said analyte indirectly by application of a calibration model to said at least one feature.

83. The method of claim 82, further comprising the step of:
preprocessing said tissue measurement.

84. The method of claim 82, further comprising any of the steps of:
detecting conditions not conducive to analyte measurement; and
detecting outliers.

85. The method of claim 82, wherein said analyte comprises any of:
water;
fat;
protein; and
glucose.

86. The method claim 82, wherein said effect comprises alteration of water distribution among body compartments.

87. A method for noninvasive measurement of a target analyte in a tissue, comprising the steps of:
collecting an analytical signal from the tissue, said collected signal comprising a tissue measurement;
preprocessing said tissue measurement;
extracting at least one feature from the analytical signal indicative of the effect of the target analyte on the probed tissue; and
either correcting a direct analyte measurement based on said at least one feature; or
calculating concentration of said analyte indirectly by application of a calibration model to said at least one feature.

88. The method of claim 87, wherein said step of preprocessing said tissue measurement comprises any of the steps of:
correcting said signal utilizing a reference;
filtering said signal;
calculating any of a first and second derivative of said signal;
normalizing said signal;
selecting portions of said signal;
scatter correcting said signal; and
translating said signal.

89. The method of claim 87, further comprising any of the steps of:
detecting conditions not conducive to analyte measurement; and
detecting outliers.

90. The method of claim 87, wherein said analyte comprises any of:
water;

fat;

protein; and glucose.

91. The method of claim 87, wherein said effect comprises alteration of water distribution among body compartments.

92. The method of claim 87, wherein said at least one feature comprise any of:
   at least a portion of a water absorbance band;
   at least a portion of a fat absorbance band; and
   at least a portion of a protein absorbance band.

* * * * *